United States Patent [19]

Hrib et al.

[11] Patent Number: 5,037,984
[45] Date of Patent: Aug. 6, 1991

[54] 3-[4-(1-SUBSTITUTED-4-PIPERAZINYL)-BUTYL]-4-THIAZOLIDINONE COMPOUNDS

[75] Inventors: Nicholas J. Hrib, Somerville; John G. Jurcak, Somerset, both of N.J.

[73] Assignee: Hoechst-Roussel Pharmaceuticals Inc., Somerville, N.J.

[21] Appl. No.: 487,328

[22] Filed: Mar. 2, 1990

Related U.S. Application Data

[63] Continuation of Ser. No. 430,688, Oct. 31, 1989, Pat. No. 4,933,453, which is a continuation-in-part of Ser. No. 123,622, Nov. 20, 1987, abandoned.

[51] Int. Cl.$^5$ .......................................... C07D 401/06
[52] U.S. Cl. .................................. 544/368; 544/230; 544/367
[58] Field of Search ............... 544/297, 230, 363, 364, 544/367, 368

[56] References Cited

FOREIGN PATENT DOCUMENTS 0125389  11/1976  Japan .................................. 544/364

Primary Examiner—C. Warren Ivy
Assistant Examiner—Zinna Northington Davis
Attorney, Agent, or Firm—Tatsuya Ikeda

[57] ABSTRACT

There are disclosed compounds of the formula

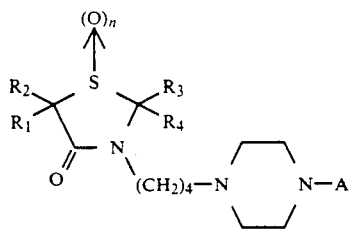

where n is 0 or 1; A is

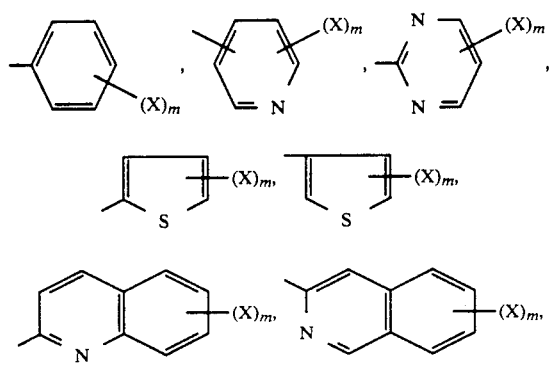

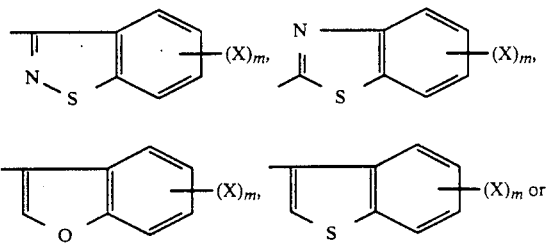

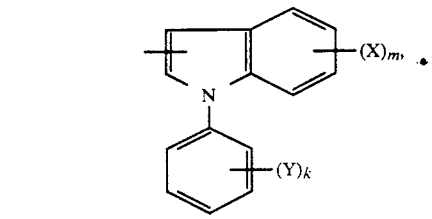

where X in each occurrence is independently hydrogen, halogen, loweralkyl hydroxy, nitro, loweralkoxy, amino, cyano, trifluoromethyl or methylthio; Y in each occurrence is independently hydrogen, halogen, loweralkyl, hydroxy, nitro, loweralkoxy, amino, cyano, trifluoromethyl or methylthio; m is 1 or 2; k is 1 or 2; $R_1$ and $R_2$ are independently hydrogen, loweralkyl,

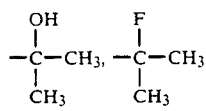

or aryl except that when $R_1$ is

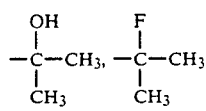

or aryl, $R_2$ is hydrogen, or alternatively $R_1 + R_2$ taken together with the carbon atom to which they are attached form a cyclopentane, cyclohexane, cycloheptane, pyran, thiopyran, indan or piperidine ring; $R_3$ and $R_4$ are independently hydrogen or loweralkyl, or alternatively $R_3 + R_4$ taken together with the carbon atom to which they are attached form a cyclopentane, cyclohexane, cycloheptane, pyran, thiopyran, pyrrolidine or piperidine ring, the term aryl signifying an unsubstituted phenyl group or a phenyl group substituted with 1, 2 or 3 substituents each of which being independently loweralkyl, loweralkoxy, hydroxy, halogen, loweralkythio, cyano, amino or trifluoromethyl, which are useful as antipsychotic, analgesic, anticonvulsant and anxiolytic agents.

43 Claims, No Drawings

3-[4-(1-SUBSTITUTED-4-PIPERAZINYL)BUTYL]-4-THIAZOLIDINONE COMPOUNDS

This is a continuation application of a prior application, Ser. No. 07/430,688 filed Oct. 31, 1989, now U.S. Pat. No. 4,933,453 which is a continuation-in-part application of a prior application Ser. No. 123,622, filed Nov. 20, 1987, now abandoned.

The present invention relates to compounds of the formula,

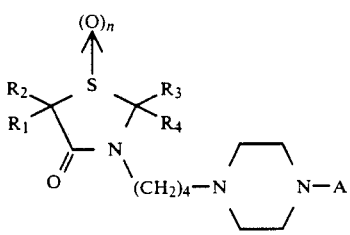

where n is 0 or 1; A is

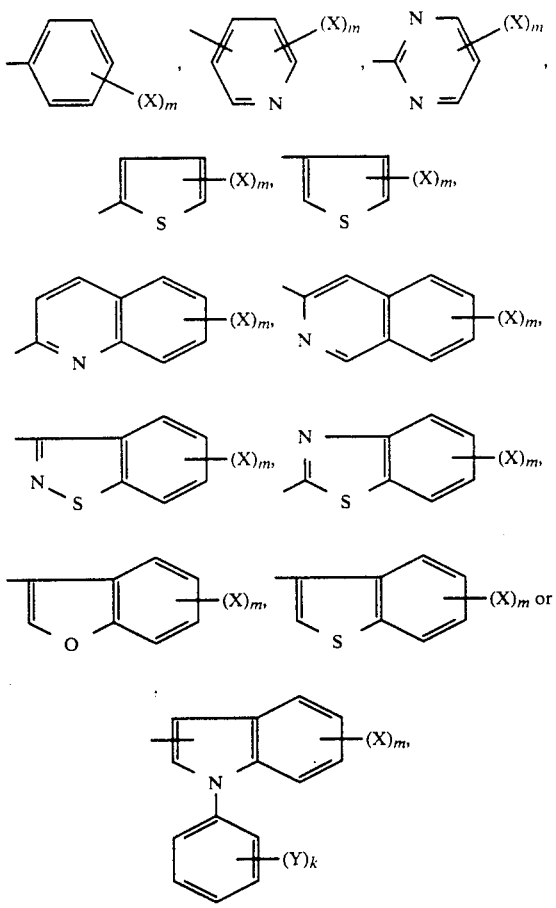

where X in each occurrence is independently hydrogen, halogen, loweralkyl, hydroxy, nitro, loweralkoxy, amino, cyano, trifluoromethyl or methylthio; Y in each occurrence is independently hydrogen, halogen, loweralkyl, hydroxy, nitro, loweralkoxy, amino, cyano, trifluoromethyl or methylthio; m is 1 or 2; k is 1 or 2; $R_1$ and $R_2$ are independently hydrogen, loweralkyl,

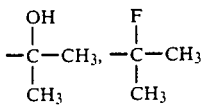

or aryl except that when $R_1$ is

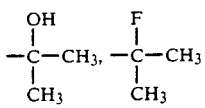

or aryl, $R_2$ is hydrogen, or alternatively $R_1 + R_2$ taken together with the carbon atom to which they are attached form a cyclopentane, cyclohexane, cycloheptane, pyran, thiopyran, indan or piperidine ring; $R_3$ and $R_4$ are independently hydrogen or loweralkyl, or alternatively $R_3 + R_4$ taken together with the carbon atom to which they are attached form a cyclopentane, cyclohexane, cycloheptane, pyran, thiopyran, pyrrolidine or piperidine ring, the term aryl signifying an unsubstituted phenyl group or a phenyl group substituted with 1, 2 or 3 substituents each of which being independently loweralkyl, loweralkoxy, hydroxy, halogen, loweralkylthio, cyano, amino or trifluoromethyl, which are useful as antipsychotic, analgesic, anticonvulsant and anxiolytic agents.

Throughout the specification and the appended claims, a given chemical formula or name shall encompass all stereo, geometrical and optical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes an alicyclic hydrocarbon group containing 3 to 7 carbon atoms.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen, loweralkylthio, cyano, amino or $CF_3$.

The compounds of this invention are prepared by utilizing one or more of the steps described below. Throughout the description of the synthetic steps, the definitions of n, m, k, A, X, Y and $R_1$ through $R_4$ are as given above unless otherwise stated or indicated.

STEP A

A compound of Formula II is reacted with 1,4-dibromobutane to afford a compound of Formula III.

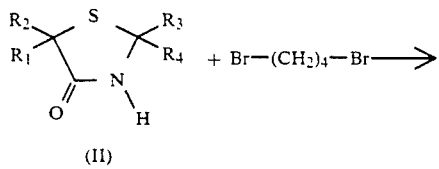

(II)

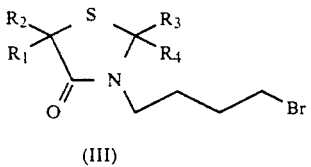

(III)

The above reaction is typically conducted in the presence of a suitable medium such as dimethylformamide or THF and a base such as potassium hydroxide, sodium hydroxide or sodium hydride at a temperature of about 23° to 70° C.

STEP B

Compound III is reacted with a compound of Formula IV to afford a compound of Formula V.

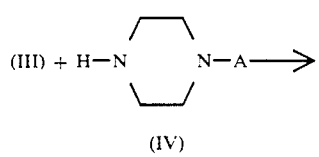

(IV)

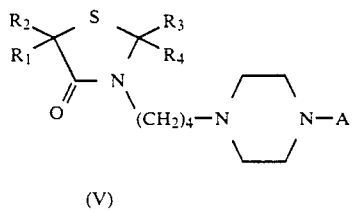

(V)

The above reaction is typically conducted in the presence of a suitable medium such as anhydrous acetonitrile, an acid scavenger such as potassium carbonate or sodium carbonate and a small amount of potassium iodide or sodium iodide at a temperature of about 20° to 100° C.

STEP C

Compound V is oxidized with a suitable oxidizing agent such as NaIO$_4$ to afford a compound of Formula VI.

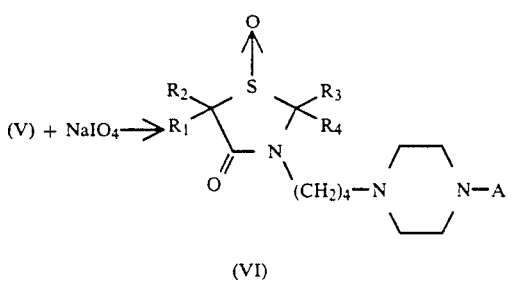

(VI)

The above reaction is typically conducted in the presence of a suitable medium such as tetrahydrofuran and water at a temperature of about −10° to 23° C.

STEP D

Compound III is oxidized in substantially the same manner as in STEP C to afford a compound of Formula VII.

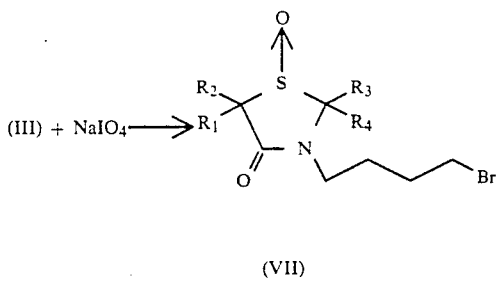

(VII)

STEP E

Compound VII is reacted with compound IV in substantially the same manner as in STEP B to afford a compound of Formula VI.

(VII)+(IV)→(VI)

STEP F

As an alternative to the foregoing scheme, one can obtain a compound of Formula VIII where P is hydrogen, loweralkyl, loweralkoxy, hydroxy, loweralkylthio or amino by reacting a compound of Formula IX with an aromatic compound of Formula X.

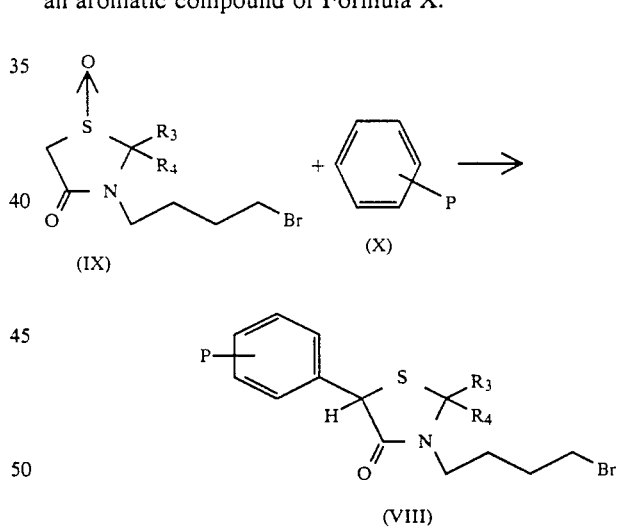

(VIII)

The above reaction is typically conducted in the presence of H$_2$SO$_4$ or p-toluenesulfonic acid at a temperature of about −10° to about 83° C.

·STEP G

As an alternative to the foregoing scheme, one can obtain a compound of Formula XI where the divalent group —R— plus the spiro carbon as combined constitutes a cyclopentane, cyclohexane, cycloheptane, pyran, thiopyran, indan or piperidine ring, in the following manner.

First, 4-thiazolidinone is reacted with t-butyldimethylsilyl chloride in a suitable solvent such as dichloromethane at a suitable temperature such as about 20°-30° C. to afford a mixture of compounds of Formulas XII and XIII. Typically the molar ratio between compound XII and compound XIII is about 70:30.

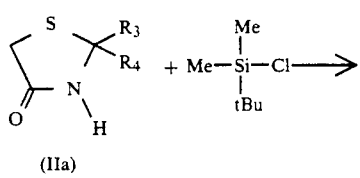

(IIa)

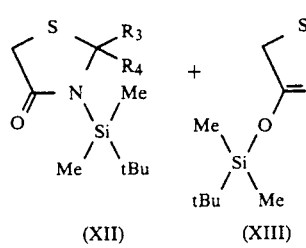

(XII)    (XIII)

The above-mentioned mixture is reacted with lithium bis(trimethylsilyl)amide and a compound of Formula XIV where R is as defined above and Hal is Br or I in a suitable medium such as tetrahydrofuran and at a low temperature such as −75° C. to −50° C. to afford compound XI.

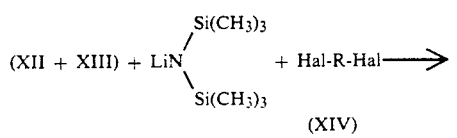

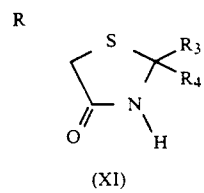

(XI)

Similarly, if one uses a mono-bromide or mono-iodide of the Formula R$_5$—Hal where R$_5$ is loweralkyl in the place of Hal—R—Hal, one can obtain a compound of Formula XV and/or XVI. In this reaction, if one desires to obtain compound XV as a predominant product, it is preferable to adjust the molar ratio between compound IIa and lithium bis(trimethylsilyl)amide to about 1:1, whereas if one desires to obtain compound XVI as a predominant product, it is preferable to adjust said molar ratio to about 1:2, also making a judicious choice in the amount of the halide compound used in each case. The two products can easily be separated from each other with the aid of a routine technique such as chromatography.

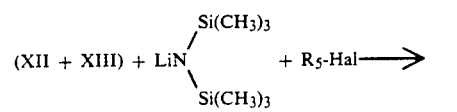

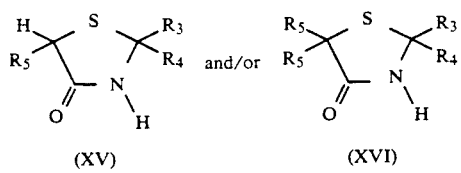

(XV)    (XVI)

STEP H

Compound IIIa (R$_1$=R$_2$=H) is allowed to react with lithium bis(trimethylsilyl)amide and compound XIV in substantially the same manner as in STEP G to afford a compound of formula XVII.

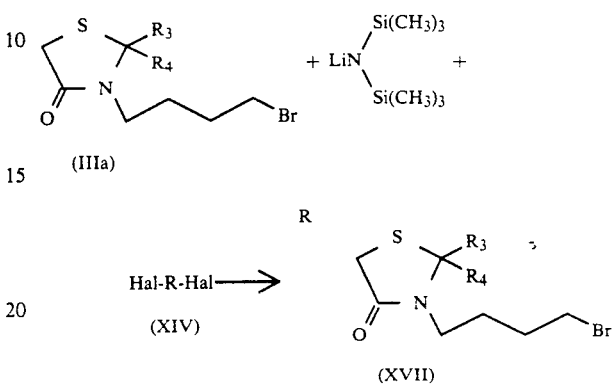

(XVII)

Similarly, if one uses R$_5$—Hal instead of Hal—R—Hal, one can obtain a compound of formula XVIII and/or XIX. In this reaction, if one desires to obtain compound XVIII as a predominant product, it is preferable to adjust the molar ratio between compound IIIa and lithium bis(trimethylsilyl)amide to about 1:1, whereas if one desires to obtain compound XIX as a predominant product, it is preferable to adjust said molar ratio to about 1:2, also making a judicious choice in the amount of the halide compound used in each case. The two products can easily be separated from each other with the aid of a routine technique such as chromatography.

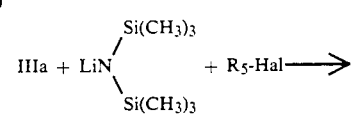

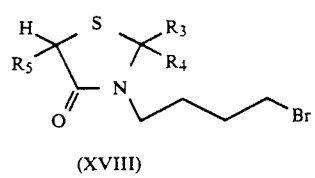

(XVIII)

and/or

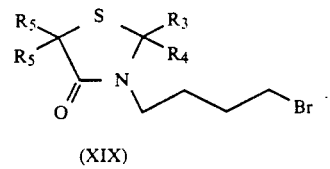

(XIX)

STEP I

Compound IIIa is allowed to react with lithium bis(trimethylsilyl)amide and about three equivalents of acetone in substantially the same manner as in STEP G to afford a compound of Formula XX.

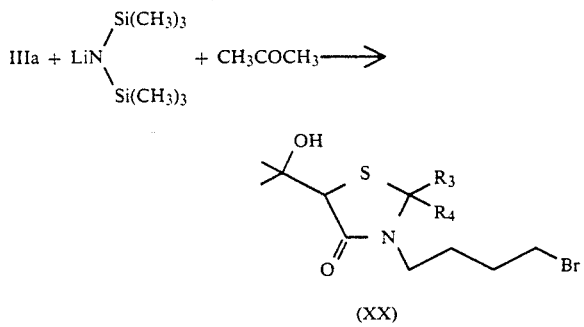

(XX)

STEP J

Compound XX is allowed to react with dimethylaminosulfur trifluoride to afford a compound of Formula XXI.

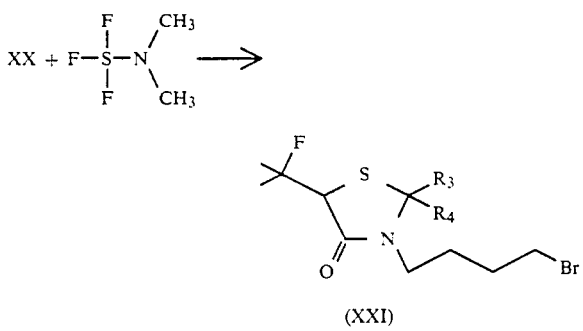

(XXI)

The above reaction is typically conducted in a suitable solvent such as dichloromethane at a temperature of −78° to 0° C.

The compounds of the present invention having Formula I are useful as antipsychotic agents.

Antipsychotic activity is determined in the climbing mice assay by methods similar to those described by P. Protais, et al., Psychopharmacol., 50, 1 (1976) and B. Costall, Eur. J. Pharmacol., 50, 39, (1978).

The subject CK-1 male mice (23–27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice with: | Score |
| --- | --- |
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless, over longer periods of time. By contrast, climbs due to mere motor stimulation usually last only a few seconds.

The climbing scores are individually totaled (maximum score: 6 per mouse over 3 readings) and the total score of the control group (vehicle intraperitoneally-apomorphine subcutaneously) is set to 100%. $ED_{50}$ values with 95% confidence limits, calculated by a linear regression analysis of some of the compounds of this invention are presented in Table 1.

TABLE 1

| Compound | Antipsychotic Activity (Climbing Mice Assay) $ED_{50}$ mg/kg ip |
| --- | --- |
| 3-[4-[1-(2-methoxyphenyl)-4-piperazinyl]-butyl]-4-thiazolidinone | 12.7 |
| 2,2-dimethyl-3-[4-[1-(2-methoxyphenyl)-4-piperazinyl]butyl-4-thiazolidinone hydrochloride hydrate | 21.9 |
| 3-[4-[1-(3-trifluoromethylphenyl)-4-piperazinyl]butyl[-4-thiazolidinone hydrochloride hemihydrate | 19.3 |
| 3-[4-[1-(2-methoxyphenyl)-4-piperazinyl]-butyl]-5-methyl-4-thiazolidinone oxalate | 12.0 |
| 3-[4-[1-(2-methylphenyl)-4-piperazinyl]-butyl]-4-thiazolidinone hydrochloride | 13.0 |
| 2,2-dimethyl-3-[4-[1-(3-methylphenyl)-4-piperazinyl]butyl-4-thiazolidinone dihydrochloride | 16.7 |
| 3-[4-[1-(1,2-benzisothiazol-3-yl)-4-piperazinyl]butyl-5,5-dimethyl-4-thiazolidinone hydrochloride (Reference Compound) | 1.4 |
| Clozapine | 8.1 |
| Sulpiride | 14.5 |

Antipsychotic response is achieved when the compounds of this invention are administered to a subject requiring such treatment as an effective oral, parenteral or intraveneous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and they do not to any extent, limit the scope or practice of the invention.

The compounds of the present invention having Formula I are also useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. Table 2 shows a result of the test of the analgesic activities of some of the compounds of this invention.

TABLE 2

| Compound | Analgesia Activity (Phenylquinone Writhing) $ED_{50}$ (mg/kg sc) |
| --- | --- |
| 2-methyl-3-[4-[1-(4-fluorophenyl)-4-piperazinyl]butyl-4-thiazolidinone hydrochloride | 1.2 |
| 3-[4-[1-(4-chlorophenyl)-4-piperazinyl]-butyl]-4-thiazolidinone hydrochloride | 2.2 |
| 3-[4-[1-(3-methoxyphenyl)-4-piperazinyl]-butyl]-4-thiazolidinone hydrochloride | 4.3 |
| 3-[4-[1-(2,3-dimethylphenyl)-4-piperazinyl]- | 2.1 |

TABLE 2-continued

| Compound | Analgesia Activity (Phenylquinone Writhing) ED$_{50}$ (mg/kg sc) |
|---|---|
| butyl]-4-thiazolidinone hydrochloride | |
| 3-[4-[1-(4-fluorophenyl)-4-piperazinyl]-butyl]-4-thiazolidinone | 2.9 |
| 3-[4-[1-(3-methylphenyl)-4-piperazinyl]-butyl]-4-thiazolidinone hydrochloride | 1.0 |
| 3-[4-[1-(2-methoxyphenyl)-4-piperazinyl]-butyl]-1,4-dioxothiazolidine (Reference Compound) | 13.2 |
| Pentazocine | 1.3 |

Compounds I of the present invention are also useful as anticonvulsant agents. The activity of the compounds is demonstrated in supramaximal electroshock assay. Groups of male mice (18-30 grams) are used. Drugs are prepared using distilled water and if insoluble, a surfactant is added. Control animals receive vehicle. Drugs are routinely administered intraperitoneally. The dosage volume is 10 ml/kg.

The animal's eyes are placed across the output terminals of an A.C. shocker that delivers 206 volts rms for 300 milliseconds. Electrode paste coats the animal's eyes at the point of contact with the terminals.

A compound is considered to give protection if the mouse does not exhibit extensor tonus. Protection is expressed as normalized percent inhibition relative to vehicle control.

Normalized % inhibition =

$$\frac{\frac{\#Rx \text{ protected}}{\#Rx \text{ tested}} - \frac{\#Control \text{ protected}}{\#Control \text{ tested}}}{1 - \frac{\#Control \text{ protected}}{\#Control \text{ tested}}} \times 100$$

A time response is carried out using 6 animals per group. Animals are tested at 30, 60, and 120 minutes postdrug. Additional time periods are tested if indicated by previous tests.

When the peak activity time has been determined, a dose response is initiated, using 10 animals per group at that time period. The ED$_{50}$ and 95% confidence interval are calculated by computerized probit analysis.

Results of the anticonvulsant activities of some of the compounds of this invention are shown in Table 3.

TABLE 3

| ANTICONVULSANT ACTIVITY | |
|---|---|
| Compound | Supramaximal Electroshock ED$_{50}$, mg/kg, ip |
| 5-phenyl-3-[4-[1-(3-trifluoromethylphenyl)-4-piperazinyl]butyl-4-thiazolidinone oxalate | 14.4 |
| 5,5-dimethyl-3-[4-[1-(3-trifluoromethylphenyl]-4-piperazinyl]butyl]-4-thiazolidinone hydrochloride (Reference Compound) | 37.3 |
| Chlordiazepoxide | 8.0 |

Compounds of the present invention are also useful as anxiolytic agents. The activity of the compounds is demonstrated in Fixed-Ratio (FR) Conflict Paradigm in Rats.

This testing paradigm is used to reveal possible "antianxiety" effects of compounds. The fixed-ratio (FR) conflict paradigm directly tests drug-induced reduction in anxiety. The method is described below.

METHOD

The FR conflict paradigm is as described by Davidson and Cook, "Effects of combined treatment with trifluoroperazine HCl and amobarbital on punished behavior in rats", Psychopharmacologia, Volume 15, 159-168 (1969). Male rats are used as test subjects. They are housed individually and food and water are available ad libitum until they are 300 to 400 g prior to the start of training. Subsequently, they are food deprived until their body weight is reduced to approximately 80% of original and it is maintained at this level by a restricted food diet.

The programming and test equipment consists of Coulbourn Instrument shockers and BRS/LVE cages within sound-attenuated environmental enclosures. The data are recorded by a computer which also controls the food and shock presentation. The cages are equipped with a hours light, a single lever, que lights, a liquid dipper, a speaker and a grid-floor connected to a shocker. Sweetened condensed milk delivered by the liquid dipper serves as the positive reinforcement for all subjects.

The subjects are trained to lever press for the milk reward in two distinct response-reward sections. In the anxiety or "conflict" segment (signaled by onset of both tone and que lights), a dipper of milk is delivered in response to each fifth lever press (FR-5 schedule of reinforcement). However, each fifth lever press during this period is also accompanied by a 40-msec pulse of aversive footshock through the grid floor. This creates a "conflict" between 1) easy access to milk reward and 2) the simultaneous presentation of a painful footshock. This conflict period is three minutes in duration.

During the other segment of this paradigm, the lever presses produce a dipper of milk only at variable intervals of time from 8 to 60 seconds with an average reward of once/30 seconds (VI-30 sec.). No shocks are ever administered during this VI phase of testing which is 4 minutes in duration.

The test procedure consists of six (nonshock) VI segments where reinforcement is available on a limited basis. Each VI period is followed by a three-minute FR-conflict phase when reinforcement is constantly available but always accompanied by an aversive footshock.

The shock level is titrated for each subject to reduce the FR responding to a total of more than 10 and less than 40 lever presses during the entire test. The rats are tested two to three days a week. Drugs are administered on the day following a control day at criteria level. After treatment, the performance is compared to the previous day's control trial. The VI responses are used to evaluate any general debilitating drug effects while the FR responses are used to evaluate any antianxiety effects as indicated by increased responding during the FR conflict period.

All test compounds are administered by i.p. injection or oral intubation in volumes of 1.0 cc/kg and the pretreat interval is usually one-half hour after i.p. administration and 60 minutes after oral administration.

An antianxiety drug will increase the FR conflict responding. It should be observed that the VI responding may also be increased.

The animals have different control VI and FR response rates and respond to antianxiety compounds at different doses. This individuality of response prevents use of group averages and does not allow meaningful $ED_{50}$ calculation. In the standard screening procedure, at least three rats that have previously shown positive anxiolytic effects with standard compounds are dosed with an experimental compound and tested. If no increase in FD responding is observed and the VI responding is not sufficiently suppressed to indicate general debilitation, then the animals are retested the following week with a greater dose. At lease one subject must show a significant increase in FR responding to indicate a positive drug effect. Drug's effects are expressed as FR conflict ratios (drug/control).

The results of this test for some of the compounds of this invention are shown in Table 4.

TABLE 4

| ANXIOLYTIC ACTIVITY | | | |
|---|---|---|---|
| Compound | dose (mg/kg i.p.) | FR conflict ratios responses | (drug/ control) rewards |
| 2,2-dimethyl-3-[4-[1-(3-methylmercaptophenyl)-4-piperazinyl]-butyl]-4-thiazolidinone dihydrochloride | 10 | 2.7 | 3.6 |
| 5,5-dimethyl-3-[4-[1-(3-trifluoromethylphenyl)-4-piperazinyl]-butyl]-4-thiazolidinone hydrochloride (reference compound) | 20 | 1.8 | 2.2 |
| Diazepam | 15 | 4.5 | 6.5 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraactic acid; buffers such as acetates; citrates or phosphates and agents for the adjustment of tonicity such as sodium chloride or dextrose. The parenteral multiple dose vials may be of glass or plastic.

Examples of the compounds of this invention include:
3-[4-[1-(2-methylphenyl)-4-piperazinyl]butyl]-4-thiazolidinone;
3-[4-[1-(3-methylphenyl)-4-piperazinyl]butyl]-4-thiazolidinone;
3-[4-[1-(2,3-dimethylphenyl)-4-piperazinyl]butyl]-4-thiazolidinone;
3-[4-[1-(2-methoxyphenyl)-4-piperazinyl]butyl]-4-thiazolidinone;
3-[4-[1-(3-methoxyphenyl)-4-piperazinyl]butyl]-4-thiazolidinone;
3-[4-[1-(4-fluorophenyl)-4-piperazinyl]butyl]-4-thiazolidinone;
3-[4-[1-(2-chlorophenyl)-4-piperazinyl]butyl]-4-thiazolidinone;
3-[4-[1-(3-chlorophenyl)-4-piperazinyl]butyl]-4-thiazolidinone;
3-[4-[1-(4-chlorophenyl)-4-piperazinyl]butyl]-4-thiazolidinone;
3-[4-[1-(3-trifluoromethylphenyl)-4-piperazinyl]butyl]-4-thiazolidinone;
3-[4-[1-(2-methoxyphenyl)-4-piperazinyl]butyl]-1,4-dioxothiazolidine;

3-[4-[1-(4-fluorophenyl)-4-piperazinyl]butyl]-1,4-dioxo-
  thiazolidine;
3-[4-[1-(2-methoxyphenyl)-4-piperazinyl]butyl]-2-meth-
  yl-4-thiazolidinone;
3-[4-[1-(4-fluorophenyl)-4-piperazinyl]butyl]-2-methyl-
  4-thiazolidinone;
3-[4-[1-(3-chlorophenyl)-4-piperazinyl]butyl]-2-methyl-
  4-thiazolidinone;
3-[4-[1-(2-methoxyphenyl)-4-piperazinyl]butyl]-5-meth-
  yl-4-thiazolidinone;
2,2-dimethyl-3-[4-[1-(3-methylphenyl)-4-piperazinyl]-
  butyl]-4-thiazolidinone;
2,2-dimethyl-3-[4-[1-(2-methoxyphenyl)-4-piperazinyl]-
  butyl]-4-thiazolidinone;
2,2-dimethyl-3-[4-[1-(3-chlorophenyl)-4-piperazinyl]-
  butyl]-4-thiazolidinone;
2,2-dimethyl-3-[4-[1-(3-trifluoromethylphenyl)-4-
  piperazinyl]butyl]-4-thiazolidinone;
2,2-dimethyl-3-[4-[1-(3-methylmercaptophenyl)-4-
  piperazinyl]butyl]-4-thiazolidinone;
5,5-dimethyl-3-[4-[1-(2-methoxyphenyl)-4-piperazinyl]-
  butyl]-4-thiazolidinone;
5,5-dimethyl-3-[4-[1-(3-trifluoromethylphenyl)-4-
  piperazinyl]butyl]-4-thiazolidinone;
5-phenyl-3-[4-[1-(3-trifluoromethylphenyl)-4-
  piperazinyl]butyl]-4-thiazolidinone;
2-methyl-3-[4-[1-(2-pyrimidinyl)-4-piperazinyl]butyl]-4-
  thiazolidinone;
3-[4-[1-(1,2-benzisothiazol-3-yl)-4-piperazinyl]butyl]-4-
  thiazolidinone;
3-[4-[1-(1,2-benzisothiazol-3-yl)-4-piperazinyl]butyl]-
  5,5-dimethyl-4-thiazolidinone;
3-[4-[1-(2-benzisothiazolyl)-4-piperazinyl]butyl]-5,5-
  dimethyl-4-thiazolidinone;
3-[4-[1-(2-quinolinyl)-4-piperazinyl]butyl]-4-thiazolidi-
  none;
5,5-dimethyl-3-[4-[1-(2-quinolinyl)-4-piperazinyl]butyl]-
  4-thiazolidinone;
2,2-dimethyl-3-[4-[1-(3-methylphenyl)-4-piperazinyl]-
  butyl]-4-thiazolidinone;
2,2-dimethyl-3-[4-[1-(2-methoxyphenyl)-4-piperazinyl]-
  butyl]-4-thiazolidinone;
2,2-dimethyl-3-[4-[1-(3-chlorophenyl)-4-piperazinyl]-
  butyl]-4-thiazolidinone;
2,2-dimethyl-3-[4-[1-(3-trifluoromethylphenyl)-4-
  piperazinyl]butyl]-4-thiazolidinone;
2,2-dimethyl-3-[4-[1-(3-methylthiophenyl)-4-
  piperazinyl]butyl]-4-thiazolidinone;
5,5-dimethyl-3-[4-[1-(2-methoxyphenyl)-4-piperazinyl]-
  butyl]-4-thiazolidinone;
5,5-dimethyl-3-[4-[1-(3-trifluoromethylphenyl)-4-
  piperazinyl]butyl]-4-thiazolidinone;
5-phenyl-3-[4-[1-(3-trifluoromethylphenyl)-4-
  piperazinyl]butyl]-4-thiazolidinone;
2-methyl-3-[4-[1-(2-pyrimidyl)-4-piperazinyl]butyl]-4-
  thiazolidinone;
3-[4-[1-(1,2-benzisothiazol-3-yl)-4-piperazinyl]butyl]-4-
  thiazolidinone;
3-[4-[1-(1,2-benzisothiazol-3-yl)-4-piperazinyl]butyl]-
  5,5-dimethyl-4-thiazolidinone;
3-[4-[1-(1,2-benzisothiazol-3-yl)-4-piperazinyl]butyl]-
  2,5,5-trimethyl-4-thiazolidinone;
3-[4-[1-(2-benzothiazolyl)-4-piperazinyl]butyl]-5,5-
  dimethyl-4-thiazolidinone;
3-[4-[1-(2-quinolinyl)-4-piperazinyl]butyl]-4-thiazolidi-
  none;
5,5-dimethyl-3-[4-[1-(2-quinolinyl)-4-piperazinyl]butyl]-
  4-thiazolidinone;

3-[4-[1-(5-fluoro-2-pyrimidinyl)-4-piperazinyl]butyl]-
  2,5,5-trimethyl-4-thiazolidinone;
3-[4-[1-(3-isoquinolinyl)-4-piperazinyl]butyl]-5,5-
  dimethyl-4-thiazolidinone;
3-[4-[1-(3-isoquinolinyl)-4-piperazinyl]butyl]-1-thia-3-
  azaspiro-[4.4]-nonan-4-one;
3-[4-[1-(1,2-benzisothiazol-3-yl)-4-piperazinyl]butyl]-1-
  thia-3-azaspiro-[4.4]-nonan-4-one;
3-[4-[1-(1,2-benzisothiazol-3-yl)-4-piperazinyl]butyl]-2-
  methyl-1-thia-3-azaspiro-[4.4]-nonan-4-one;
3-[4-[1-(1,2-benzisothiazol-3-yl)-4-piperazinyl]butyl]-
  2,2-dimethyl-1-thia-3-azaspiro-[4.4]-nonan-4-one;
3-[4-[1-(3-trifluoromethylphenyl)-4-piperazinyl]butyl]-
  5,5-dimethyl-4-thiazolidinone;
3-[4-[1-(1,2-benzisothiazol-3-yl)-4-piperazinyl]butyl]-
  2,2-dimethyl-4-thiazolidinone;
3-[4-[1-(1,2-benzisothiazol-3-yl)-4-piperazinyl]butyl]-
  2,2,5,5-tetramethyl-4-thiazolidinone;
3-[3-[1-(1,2-benzisothiazol-3-yl)-4-piperazinyl]propyl]-
  5-methyl-4-thiazolidinone;
3-[4-[1-(2-methylphenyl)-4-piperazinyl]butyl]-5,5-
  dimethyl-4-thiazolidinone;
3-[4-[1-(2,3-dimethylphenyl)-4-piperazinyl]butyl]-5,5-
  dimethyl-4-thiazolidinone;
3-[4-[1-(1-phenyl-1H-indol-3-yl)-4-piperazinyl]butyl]-
  5,5-dimethyl-4-thiazolidinone;
3-[4-[1-[1-(4-fluorophenyl)-1H-indol-3-yl]-4-
  piperazinyl]butyl]-5,5-dimethyl-4-thiazolidinone;
3-[4-[1-(benzo[b]thiophen-3-yl)-4-piperazinyl]butyl]-1-
  thia-3-azaspiro[4.4]-one;
3-[4-[1-(1-phenyl-1H-indol-3-yl)-4-piperazinyl]butyl]-2-
  methyl-1-thia-3-azaspiro[4.4]nonan-4-one;
3-[4-(1-benzo[b]thiophen-3-yl)-4-piperazinyl)butyl]-1-
  thia-3-azaspiro[4.5]decan-4-one;
3-[4-[1-(1-phenyl-1H-indol-3-yl)-4-piperazinyl]butyl]-1-
  thia-3-azaspiro[5.4]decan-4-one;
3-[4-[1-[1-(4-fluorophenyl)-1H-indol-3-yl]-4-
  piperazinyl]butyl]-1-thia-3-azaspiro[4.5]decan-4-one;
3-[4-[1-(1,2-benzisothiazol-3-yl)-4-piperazinyl]butyl]-5-
  butyl-4-thiazolidinone;
3-[4-[1-(2-(5-fluoropyrimidinyl))-4-piperazinyl]butyl]-
  5,5-dimethyl-4-thiazolidinone;
3-[4-[1-(2-(6-fluoropyridinyl))-4-piperazinyl]butyl]-4-
  thiazolidinone;
2,5,5-trimethyl-3-[4-[1-(2-(3-cyanopyridinyl))-4-
  piperazinyl]butyl]-4-thiazolidinone;
3-[4-[1-(benzo[b]furan-3-yl)-4-piperazinyl]butyl]-5-
  ethyl-4-thiazolidinone;
3-[4-[1-(4-pyridinyl)-4-piperazinyl]butyl]-1-thia-3-azas-
  piro[4.4]nonan-4-one;
3-[4-[1-(6-fluorobenzo[b]furan-3-yl)-4-piperazinyl]-
  butyl]-5-methyl-4-thiazolidinone;
3-[4-[1-(1,2-benzisothiazol-3-yl)-4-piperazinyl]butyl]-1-
  thia-3-azaspiro[6.4]undecan-4-one;
3-[4-[1-(6-chloro-1,2-benzisothiazol-3-yl)-4-
  piperazinyl]butyl]-5-(2-hydroxyisopropyl)-4-
  thiazolidinone;
3-[4-[1-(2-(3-chloropyridinyl)-4-piperazinyl]butyl]-5-(2-
  fluoroisopropyl)-4-thiazolidinone;
2,5,5-trimethyl-3-[4-[1-(2-(5-chlorothiophenyl))-4-
  piperazinyl]butyl]-4-thiazolidinone;
2-methyl-3-[4-[1-(2-(5-fluoropyrimidinyl))-4-
  piperazinyl]butyl]-1-thia-3-azaspiro[4.4]nonan-4-one;
2,5,5-trimethyl-3-[4-[1-(6-chloro-1,2-benzisothiazol-3-
  yl)-4-piperazinyl]butyl]-4-thiazolidinone;
2-methyl-3-[4-[1-(1-phenyl-6-fluoro-1H-indol-3-yl)-4-
  piperazinyl]butyl]-1-thia-3-azaspiro[4.4]nonan-4-one;

2,5,5-trimethyl-3-[4-[1-(6-fluorobenzo[b]thiophen-3-yl)-4-piperazinyl]butyl]-4-thiazolidinone;
3-[4-[1-(1,2-benzisothiazol-3-yl)-4-piperazinyl]butyl]-5-(2-hydroxyisopropyl)-4-thiazolidinone;
3-[4-[1-(1,2-benzisothiazol-3-yl)-4-piperazinyl]butyl]-spiro[1H-indene-2,5-thiazolidine]-2,3-dihydro-4-one;
3-(4-(1-[1,2-benzisothiazol-3-yl]-4-piperazinyl)butyl)-5-methyl-4-thiazolidinone;
3-(4-(1-(6-fluorobenzo[b]thiophen-3-yl)-4-piperazinyl)-butyl-5-(2-hydroxyisopropyl)-4-thiazolidinone;
3-(4-(1-(1,2-benzisothiazol-3-yl)-4-piperazinyl)butyl)-5-(2,2,2-trifluoroethyl)-4-thiazolidinone;
3-(4-(1-(3-methylphenyl)-4-piperazinyl)butyl)-5,5-dimethyl-4-thiazolidinone;
3-(4-(1-(6-chlorobenzo[b]thiophen-3-yl)-4-piperazinyl)-butyl)-2,5,5-trimethyl-4-thiazolidinone;
3-(4-(1-[1-phenyl-1H-indol-3-yl]-4-piperazinyl)butyl)-2,5,5-trimethyl-4-thiazolidinone;
3-(4-(1-(1-(4-fluorophenyl)-1H-indol-3-yl]-4-piperazinyl)butyl)-2,5,5-trimethyl-4-thiazolidinone;
3-(4-(1-[3-methylphenyl]-4-piperazinyl)butyl)-2,2,5,5-tetramethyl-4-thiazolidinone;
3-(4-(1-(2-methoxyphenyl)-4-piperazinyl)butyl)-2,2,5,5-tetramethyl-4-thiazolidinone;
3-(4-(1-(2-methoxyphenyl)-4-piperazinyl)butyl)-1-thia-3-azaspiro[4.4]nonan-4-one;
3-(4-(1-(benzo[b]thiophen-3-yl)-4-piperazinyl)butyl)-1-thia-3-azaspiro[4.4]nonan-4-one;
3-[4-[1-(1,2-benzisothiazol-3-yl)-4-piperazinyl]butyl]-1-thia-3-azaspiro[4.4]nonan-4-one;
3-(4-(1-(1,1-dioxo-1,2-benzisothiazol-3-yl-1)-4-piperazinyl)butyl)-1-thia-3-azaspiro[4.4]nonan-4-one;
3-(4-(1-(6-fluorobenzo[b]thiophen-3-yl)-4-piperazinyl)-butyl)-2-methyl-3-azaspiro[4.4]nonan-4-one;
3-(4-(1-(6-chlorobenzo[b]thiophen-3-yl)-4-piperazinyl)-butyl)-2-methyl-1-thia-3-azaspiro[4.4]nonan-4-one;
3-(4-(1-(1,2-benzisothiazol-3-yl)-4-piperazinyl)butyl)-2-methyl-1-thia-3-azaspiro[4.4]nonan-4-one;
3-(4-(1-[1,2-benzisothiazol-3-yl]-4-piperazinyl)butyl)-1-thia-3-azaspiro[4.5]decan-4-one;
3-[4-[1-(6-chloro-1,2-benzisothiazol-3-yl)-4-piperazinyl]butyl]-1-thia-3-azaspiro[4.5]decan-4-one;

The following examples are presented in order to illustrate this invention.

EXAMPLE 1

5,5-Dimethyl-4-thiazolidinone

A solution of 4-thiazolidinone (10.0 g), t-butyldimethylsilyl chloride (16.40 g), triethylamine (20.3 mL) and $CH_2Cl_2$ (250 mL) was stirred at room temperature under nitrogen. After 15 min. the reaction mixture became cloudy. After 27 h, $Et_2O$ (200 mL) was added, the mixture was filtered through $Al_2O_3$ and the triethylammonium chloride cake washed with $Et_2O$ (350 mL). The combined filtrate was concentrated in vacuo to a cloudy oil (26.1 g). Distillation of the cloudy oil gave 19.63 g of a clear liquid, bp. 73°–75° C. at 0.30 mmHg. Spectral data showed oil to be a 70:30 mixture of N- and O- silylated material, namely, 3-t-butyldimethylsilyl-4-thiazolidinone and 4-t-butyldimethylsilyloxy-3-thiazoline.

To a $-45°$ C. solution of lithium bis(trimethylsilyl)amide (80.0 mmol) and tetrahydrofuran (80 mL) under $N_2$ was added a 0° C. solution prepared from 7.91 g of the above-mentioned 70:30 mixture between 3-t-butyl-dimethylsilyl-4-thiazolidinone and 4-t-butyldimethyl-silyloxy-3-thiazoline, iodomethane (11.36 g) and THF (30 mL). The reaction mixture was stirred at $-40°$ C. to $-50°$ C. for 70 min. TLC analysis (silica gel, 7% ethyl acetate/hexane) showed a trace of starting material, $R_f$=0.31, and a major product, $R_f$=0.50, along with material at the origin. The reaction mixture was removed from the cold bath and quenched with 2N HCl (120 mL). The aqueous mixture was stirred rapidly for 1.5 h. TLC analysis (silica gel, ethyl acetate) showed a major product, $R_f$=0.45, and 4-thiazolidinone, $R_f$=0.31, after visualization with iodine. The aqueous mixture was evaporated in vacuo to remove tetrahydrofuran and the resultant aqueous mixture was extracted with dichloromethane (5×70 mL). The combined extracts were washed with brine (150 mL), dried over $Na_2SO_4$ and concentrated in vacuo to 3.88 g of a dark solid. The crude product was flash chromatographed (180 g silica gel, 10% hexane/ethyl acetate) to give 2.28 g of an off-white solid. It was recrystallized from diethyl ether (25 ml) to yield 1.12 g of crystals, mp 105°–107° C.

ANALYSIS: Calculated for $C_5H_9NOS$: 45.77%C; 6.92%H; 10.68%N. Found: 45.74%C; 6.88%H; 10.67%N.

EXAMPLE 2

1-Thia-3-azaspiro[4.4]nonane-4-one

To a $-75°$ C. ($CO_2$/isopropanol bath) mixture of lithium bis(trimethylsilyl)amide (0.151 mol) and THF (151 mL) under nitrogen was added a 0° C. solution prepared from 14.95 g of a 70:30 mixture between 3-t-butyldimethylsilyl-4-oxothiazolidine and 4-t-butyldimethylsilyloxy-3-thiazoline (prepared as in Example 1) and 1,4-dibromobutane (14.85 g) in THF (50 mL) over a period of 0.5 h. The resultant homogeneous solution was stirred at $-75°$ C. for 70 min. TLC analysis (silica gel, 10% EtOAc/hexane) showed a major product, ($R_f$=0.48) and a minor product ($R_f$=0.31). The reaction mixture was removed from the cold bath and acidified with 2N HCl (200 mL). The aqueous mixture was stirred rapidly for 3.5 h at room temperature, placed in vacuo to remove the tetrahydrofuran, and extracted with dichloromethane (5×75 mL). The organic extracts were dried over $Na_2SO_4$ and concentrated in vacuo to yield 14.2 g of an oily solid. The crude oily product was chromatographed (Waters Prep 500, 2 silica gel columns, 20% hexane/ethyl acetate) to give 2.75 g of a white solid ($R_f$=0.45). Recrystallization from diethylether/hexane yielded 1.37 g of a crystalline solid, mp 92°–94° C.

ANALYSIS: Calculated for $C_7H_{11}NOS$: 53.47%C; 7.05%H; 8.91%N. Found: 53.41%C; 7.01%H; 8.88%N.

EXAMPLE 3

3-(4-Bromobutyl)-4-thiazolidinone

A mixture of 4-thiazolidinone (25 g), dimethylformamide (DMF hereafter, 500 ml) and KOH (27.16 g) was stirred under $N_2$ at room temperature for 1.5 h. To the resulting mixture was added 1,4-dibromobutane (101 ml), which rapidly caused the reaction mixture to turn milkyl white. Stirring was continued at room temperature for 44 h. The reaction mixture was poured into $H_2O$ (1000 ml) and the aqueous mixture was extracted with ethyl acetate (EtOAc hereafter, 3×300 ml). The combined extracts were washed successively with $H_2O$ (300 ml) and brine (300 ml), dried over $Na_2SO_4$, and concentrated in vacuo to an amber oil. HPLC (high performance liquid chromatography) of a 44.95 g aliquot yielded 7.15 g of an oil which upon distillation yielded a clear liquid, b.p. 134°–137° C./0.12 mm Hg.

ANALYSIS: Calculated for $C_7H_{12}BrNOS$: 35.30%C; 5.08%H; 5.88%N. Found: 35.24%C; 5.09%H; 5.83%N.

EXAMPLE 4

3-(4-Bromobutyl)-5,5-dimethyl-4-thiazolidinone

To a −75° C. (CO$_2$/isopropanol bath) mixture of lithium bis(trimethylsilyl)amide and tetrahydrofuran (102 mL) under nitrogen was added a 0° C. solution consisting of 3-(4-bromobutyl)-4-thiazolidinone (11.65 g), iodomethane (20.8 g) and tetrahydrofuran (20 mL) over a period of 20 min. The resultant solution was stirred at −75° C. for 25 min. TLC analysis (silica gel, 32% EtOAc/hexane) of a small aliquot acidified with 1N HCl showed the absence of a starting bromide and the presence of a major product, $R_f \approx 0.41$. The reaction mixture was removed from the cold bath and acidified with 1N HCl (200 mL). The aqueous mixture was extracted with diethyl ether (3×175 mL). The combined extracts were washed with brine (200 ml), dried over Na$_2$SO$_4$ and concentrated in vacuo to an oil. The crude oil was chromatographed (Waters Prep 500, 2 silica gel columns, 30% EtOAc/hexane) to give 11.02 g of an oil as the major product, $R_f \approx 0.41$. A sample (2.80 g) of this was distilled using a short path head yielding 2.68 g of a faint yellow oil (bath temperature 90°–100° C./0.05 mm Hg).

ANALYSIS: Calculated for $C_9H_{16}BrNOS$: 40.60%C; 6.06%H; 5.26%N. Found: 40.64%C; 6.12%H; 5.20%N.

EXAMPLE 5

2-Methyl-3-(4-bromobutyl)-4-thiazolidinone

To a stirred suspension of 2-methyl-4-thiazolidinone (20 g) in 500 ml of anhydrous DMF under N$_2$ was added in one portion potassium hydroxide (19.1 g). Stirring was continued for ½ h resulting in a yellow solution. At this time 1,4-dibromobutane (61 ml) was added in one portion.

After 1 hour, no starting material remained as judged by TLC [silica, EtOAc]. The mixture was quenched in 600 ml of H$_2$O and extracted exhaustively with EtOAc. The organic fractions were washed twice with H$_2$O, dried over MgSO$_4$ and concentrated in vacuo. HPLC of the residue, using a 3:1 hexane/EtOAc eluent, provided 16.02 g of product as an oil which was homogeneous by TLC [silica 2:1 hexane/EtOAc].

ANALYSIS: Calculated for $C_8H_{14}BrNOS$: 38.10%C; 5.60%H; 5.55%N. Found: 37.81%C; 5.78%H; 5.39%N.

EXAMPLE 6

3-(4-Bromobutyl)-2,2-dimethyl-4-thiazolidinone

A solution of 2,2-dimethyl-4-thiazolidinone (5.00 g) in DMF (30 ml) was added dropwise to a suspension of NaH (0.0419 mole, previously washed with hexane) in DMF (30 ml) under N$_2$. The resultant mixture was stirred for 1 h, transferred to an addition funnel and added dropwise to a solution of 1,4-dibromobutane (18.10 g) in DMF (50 ml) over a period of 40 min. The resultant solution was heated at 70° C. under N$_2$ for 120 hr. TLC analysis (silica gel, 10% EtOAc/CH$_2$Cl$_2$) showed the presence of one major product and starting thiazolidinone. The reaction mixture was cooled to room temperature and poured into H$_2$O (400 ml), and the aqueous mixture extracted with EtOAc (3×175 ml). The combined extracts were washed with H$_2$O (200 ml) and brine (200 ml), dried over Na$_2$SO$_4$, and concentrated in vacuo to an oily residue (20.44 g). The crude product was purified by HPLC (4% EtOAc/CH$_2$Cl$_2$) to yield 5.91 g of oil. Distillation in vacuo afforded 4.61 g of a faint yellowish oil, bp 133°–136° C./0.70 mm Hg.

ANALYSIS: Calculated for $C_9H_{16}BrNOS$: 40.60%C; 6.06%H; 5.26%N. Found: 40.63%C; 6.03%H; 5.17%N.

EXAMPLE 7

3-(4-Bromobutyl)-5-methyl-4-thiazolidinone

To 12.35 g of 5-methyl-4-thiazolidinone placed in a 500 ml round bottom flask was added 210 ml of DMF and the mixture stirred for 3.5 h. An additional 30 ml of DMF was added and the mixture stirred for 10 minutes and thereafter 11.8 g of KOH was added all at once. The resultant solution was stirred for 0.5 h at room temperature and thereafter 38 ml of 1,4-dibromobutane was added rapidly. The mixture was stirred at room temperature overnight. After 24 hours of stirring at room temperature, the reaction mixture was poured into 600 ml of water and the resultant mixture extracted with EtOAc (2×175 ml). The combined EtOAc layers were washed successively with water (200 ml) and brine (150 ml), dried over MgSO$_4$ and concentrated in vacuo to 49.68 g of oil. After removal of DMF by vacuum distillation, the residual oil was purified by flash chromatography (silica gel column) to obtain the desired product.

EXAMPLE 8

3-(4-Bromobutyl)-5-phenyl-4-thiazolidinone

To a rapidly stirred mixture of H$_2$SO$_4$ (73 ml) and benzene (30 ml) was added a mixture of 3-(4-bromobutyl)-1,4-dioxothiazolidine (13.66 g, prepared from 3-(4-bromobutyl)-4-thiazolidinone by oxidation with NaIO$_4$ conducted in substantially the same manner as in Example 17 described later), benzene (120 ml) and CH$_2$Cl$_2$ (10 ml). The exothermic reaction was cooled with an ice/water bath and stirring was continued for 50 minutes, during which the mixture was gradually warmed to room temperature. The mixture was poured onto 750 g of ice and extracted with CH$_2$Cl$_2$ (4×150 ml). The combined extracts were washed with 5% NaHCO$_3$ (300 ml), H$_2$O (300 ml) and brine (300 ml), dried over Na$_2$SO$_4$, and concentrated in vacuo to yield 15.00 g of an oil. TLC analysis (silica gel, 40% EtOAc/hexane) showed a major product with Rf=0.37. The crude oil was purified by HPLC chromatography, whereupon the product solidified. It (6.17 g) was recrystallized from Et$_2$O to yield 2.7 g of a crystalline solid, mp 48°–50° C.

ANALYSIS: Calculated for $C_{13}H_{16}BrNOS$: 49.68%C; 5.13%H; 4.46%N. Found: 49.73%C; 5.26%H; 4.78%N.

EXAMPLE 9

3-(4-Bromobutyl)-5-(4-methoxyphenyl)-4-thiazolidinone

A mixture of p-toluenesulfonic acid monohydrate (6.56 g) and 1,2-dichloroethane (100 mL) was heated to reflux using an apparatus equipped with a water separator. Approximately 70 mL of distillate was removed and the reddish solution was cooled to room temperature. To this solution was added anisole (9.30 g), followed by a solution of 3-(4-bromobutyl)-1,4-dioxothiazolidine (4.38 g) and 1,2-dichloroethane (60 mL) and the resultant mixture was heated to reflux (bath temperature=120° C.). Approximately 60 mL of distillate was removed, another 30 mL of 1,2-dichloroethane was added, and the reaction allowed to reflux. Another 30 mL of distillate was removed, the reaction mixture was cooled to ambient temperature and poured into H$_2$O (60 mL). The aqueous mixture was extracted with Et$_2$O (4×40 mL) and the combined extracts were washed with brine (70 mL), dried (Na$_2$SO$_4$) and concentrated in vacuo to a yellow liquid. TLC analysis (silica gel, 2% EtOAc/CH$_2$Cl$_2$) of the liquid showed an elongated spot, R$_f$=0.33. The yellow liquid was chromatographed to afford 3.70 g of oil, a mixture of o- and p- isomers as determined by proton NMR and 1.55 g of the pure p-isomer (R$_f$=0.48, silica gel, 3% EtOAc/CH$_2$Cl$_2$). The latter was dried at room temperature/0.1 mmHg for 100 h.

ANALYSIS: Calculated for C$_{14}$H$_{18}$BrNO$_2$S: 48.84%C; 5.27%H; 4.07%N. Found: 48.61%C; 5.40%H; 3.97%N.

EXAMPLE 10

3-[4-[1-(2-Methylphenyl)-4-piperazinyl]butyl]-4-thiazolidinone hydrochloride A mixture of 3-(4-bromobutyl)-4-thiazolidinone (4.10 g), 1-(2-methylphenyl)piperazine (5.6 g), K$_2$CO$_3$ (7.13 g), NaI (300 mg) and CH$_3$CN (200 ml) was refluxed (oil bath temperature 95° C.) under N$_2$ for 20 h. TLC analysis (silica gel, 20% MeOH/EtOAc) showed one major product at Rf=0.37, and a trace of starting bromide at Rf=0.67. The mixture was cooled to room temperature, EtOAc (100 ml) was added and the mixture was filtered. The filtrate was concentrated in vacuo to an oil which was triturated with EtOAc to precipitate a solid. The mixture was filtered and the filtrate concentrated in vacuo to an oil. The oil was chromatographed by HPLC over silica gel and the purified oil (5.42 g) was dissolved in Et$_2$O (600 ml). The salt of this amine was precipitated by the addition of an HCl/Et$_2$O solution until pH=1, yielding 5.50 g of crystals. The crude salt (4.00 g) was recrystallized from EtOH/EtOAc to yield 3.13 g of a crystal solid, mp 207°-209° C.

ANALYSIS: Calculated for C$_{18}$H$_{27}$N$_3$OS.HCl: 58.44%C; 7.63%H; 11.36%N; 9.58%Cl. Found: 58.35%C; 7.56%H; 11.35%N; 9.69%Cl.

EXAMPLE 11

3-[4-[1-(3-Methylphenyl)-4-piperazinyl]butyl]-4-thiazolidinone hydrochloride A mixture of 3-(4-bromobutyl)-4-thiazolidinone (4.00 g), 1-(3-tolyl)piperazine dihydrochloride (4.23 g), K$_2$CO$_3$ (9.40 g), NaI (200 mg) and CH$_3$CN (150 ml) was heated at reflux (bath temperature 90° C.) under N$_2$ for 52 h. TLC analysis (silica gel, 7.5% EtOH/CH$_2$Cl$_2$) showed some starting bromide at Rf=0.57 and a major product at Rf=0.41. The reaction mixture was cooled to room temperature, filtered, and the filtrate concentrated in vacuo to an oil. The crude product was flash chromatographed (silica gel) to yield 3.40 g of a heavy oil. TLC analysis (silica gel) of this showed the presence of starting bromide. The oil solidified on cooling and the resultant solid was triturated with Et$_2$O/hexane yielding 2.48 g of solid, mp 69°-73° C. Flash chromatography (silica gel) of the crude product afforded 2.10 g of a purified solid, mp 70°-72° C. The salt of this amine was prepared in ether by the addition of an HCl/Et$_2$O solution. It was recrystallized from EtOH/EtOAc to provide 1.55 g of white crystals, mp 201°-203° C.

ANALYSIS: Calculated for C$_{18}$H$_{27}$N$_3$OS.HCl: 58.44%C; 7.63%H; 11.36%N. Found: 58.44%C; 7.73%H; 11.31%N.

EXAMPLE 12

3-[4-[1-(2,3-Dimethylphenyl)-4-piperazinyl]butyl]-4-thiazolidinone hydrochloride To a solution of 3-(4-bromobutyl)-4-thiazolidinone (4.0 g) and 1-(2,3-dimethylphenyl)piperazine hydrochloride (3.8 g) in 100 ml of anhydrous CH$_3$CN were added K$_2$CO$_3$ (9.3 g) and NaI (200 mg). The mixture was heated to 80° with stirring under N$_2$.

After 18 hours the mixture was cooled to room temperature and filtered. The filtrate was concentrated in vacuo, taken up in EtOAc and filtered again. The solvent was removed in vacuo and the residue chromatographed on silica using 98:2 EtOAc/CH$_3$OH as an eluent. Fractions containing the pure product were combined and concentrated to give 3.36 g of free amine.

The HCl salt of this amine was precipitated from Et$_2$O to provide 3.118 g of product, mp 228°-230° C.

ANALYSIS: Calculated for C$_{19}$H$_{29}$N$_3$OS.HCl: 59.43%C; 7.87%H; 10.94%N. Found: 59.34%C; 8.07%H; 10.93%N.

EXAMPLE 13

3-[4-[1-(2-Methoxyphenyl)-4-piperazinyl]butyl]-4-thiazolidinone

A suspension of 3-(4-bromobutyl)-4-thiazolidinone (3.0 g), 1-(2-methoxyphenyl)piperazine (2.43 g), anhydrous K$_2$CO$_3$ (3 g) and NaI (200 mg) in 100 ml of anhydrous CH$_3$CN was heated to reflux under N$_2$. After 18 hours the mixture was cooled to room temperature and filtered. The filtrate was concentrated in vacuo, and the residue taken up and chromatographed (silica, EtOAc eluent) to provide 3.49 g of product as a white solid, mp 80°-81° C.

ANALYSIS: Calculated for C$_{18}$H$_{27}$N$_3$O$_2$S: 61.86%C; 7.79%H; 12.02%N. Found: 62.07%C; 7.89%H; 11.95%N.

EXAMPLE 14

3-[4-[1-(3-Methoxyphenyl)-4-piperazinyl]butyl]-4-thiazolidinone hydrochloride To a solution of 3-(4-bromobutyl)-4-thiazolidinone (3.0 g) and 1-(3-methoxyphenyl)piperazine dihydrochloride (3.34 g) in 100 ml of anhydrous CH$_3$CN were added K$_2$CO$_3$ (8.7 g) and NaI (200 mg). The mixture was heated to 80° with stirring under N$_2$.

After 18 hours the mixture was cooled to room temperature and filtered. The CH$_3$CN was removed in vacuo and the residue was chromatographed on silica using 98:2 EtOAc/CH$_3$OH as the eluent. The fractions containing the desired product were combined, concentrated in vacuo and taken up in anhydrous Et$_2$O.

The HCl salt of the free amine was precipitated from Et$_2$O, collected and dried to provide 2.850 g of product, mp 161°-162° C.

ANALYSIS: Calculated for C$_{18}$H$_{27}$N$_3$O$_2$S.HCl: 56.02%C; 7.31%H; 10.89%N. Found: 55.66%C; 7.37%H; 10.83%N.

EXAMPLE 15

3-[4-[1-(4-Fluorophenyl)-4-piperazinyl]butyl]-4-thiazolidinone

A mixture of 3-(4-bromobutyl)-4-thiazolidinone (4.01 g), 1-(4-fluorophenyl)piperazine (3.35 g), $K_2CO_3$ (4.64 g), NaI (150 mg) and $CH_3CN$ (150 ml) was heated at 100° C. (bath temperature) under $N_2$ for 18 h. TLC analysis (silica gel, 8% $MeOH/CHCl_3$) showed one major product at $R_f=0.36$, and the absence of starting bromide. The reaction mixture was cooled to room temperature and concentrated in vacuo to an oil which was taken up in EtOAc. The mixture was filtered to remove the precipitate and the filtrate concentrated in vacuo to an amber oil which solidified under vacuum. The solid (5.86 g) was dissolved in $CHCl_3$ and flash chromatographed (silica gel) and thereafter recrystallized from hexane/$CH_2Cl_2$ to yield in two crops 3.93 g of white crystals, mp 83°–85° C. TLC analysis showed a trace of slower moving impurity. Recrystallization from hexane/$CH_2Cl_2$ afforded 3.1 g of white needles which were still slightly impure by TLC. The material was again flash chromatographed (silica gel) and recrystallized from hexane/$CH_2Cl_2$ to give 2.67 g of pure product, mp 84°–85° C.

ANALYSIS: Calculated for $C_{17}H_{24}N_3OSF$: 60.50%C; 7.17%H; 12.45%N. Found: 60.55%C; 7.19%H; 12.43%N.

EXAMPLE 16

3-[4-[1-(2-Chlorophenyl)-4-piperazinyl]butyl]-4-thiazolidinone hydrochloride A mixture of 3-(4-bromobutyl)-4-thiazolidinone (4.02 g), 1-(2-chlorophenyl)piperazine (3.94 g), $K_2CO_3$ (7.01 g), NaI (250 mg) and $CH_3CN$ (130 ml) was heated at 100° C. (bath temperature) for 20 hours under $N_2$. The mixture was cooled to room temperature, filtered and concentrated in vacuo to an amber oil. The oil was triturated with EtOAc and the mixture was filtered. The filtrate was concentrated in vacuo to 6.07 g of an oil residue which was flash chromatographed (silica gel) to yield 4.47 g of an oily product. The HCl salt of this amine was prepared in ether with ethereal HCl to give 3.77 g of a white solid, mp 182°–185° C. The solid was recrystallized from EtOAc (130 ml)/$CH_2Cl_2$ (30 ml) yielding 3.01 g of white needles, mp 185°–187° C.

ANALYSIS: Calculated for $C_{17}H_{24}N_3ClOS.HCl$: 52.30%C; 6.46%H; 10.76%N. Found: 52.28%C; 6.51%H; 10.64%N.

EXAMPLE 17

3-[4-[1-(3-Chlorophenyl)-4-piperazinyl]butyl]-4-thiazolidinone hydrochloride To a solution of 3-(4-bromobutyl)-4-thiazolidinone (3.0 g) and 1-(2-chlorophenyl)piperazine dihydrochloride (3.4 g) in 100 ml of anhydrous $CH_3CN$ were added $K_2CO_3$ (8.7 g) and NaI (200 mg). The mixture was heated at 80° with stirring under $N_2$.

After 18 hours the mixture was cooled to room temperature and filtered. The filtrate was concentrated in vacuo, taken up in EtOAc and chromatographed on silica using EtOAc/$CH_3OH$ (95:5) as the eluent. The fractions containing the product were combined and concentrated in vacuo.

The HCl salt of the amine was precipitated from $Et_2O$, dried and collected to provide 2.7 g of product, mp 157°–159° C.

ANALYSIS: Calculated for $C_{17}H_{24}ClN_3OS.HCl$: 52.30%C; 6.45%H; 10.76%N. Found: 51.93%C; 6.80%H; 10.81%N.

EXAMPLE 18

3-[4-[1-(4-Chlorophenyl)-4-piperazinyl]butyl]-4-thiazolidinone hydrochloride To a solution of 3-(4-bromobutyl)-4-thiazolidinone (3.0 g) and 1-(4-chlorophenyl)piperazine dihydrochloride (3.4 g) in 100 ml of anhydrous $CH_3CN$ were added $K_2CO_3$ (8.7 g) and KI (200 mg). The mixture was heated to 80° with stirring under $N_2$.

After 18 hours the mixture was cooled to room temperature and filtered. The filtrate was concentrated in vacuo, taken up in EtOAc and chromatographed on silica using EtOAc/$CH_3OH$ (95:5) as the eluent. The fractions containing the product were combined and concentrated in vacuo.

The HCl salt of the amine was precipitated from $Et_2O$, dried and collected to provide 2.33 g of product, mp 186°–188° C. (dec).

ANALYSIS: Calculated for $C_{17}H_{24}ClN_3OS.HCl$: 52.30%C; 6.45%H; 10.76%N. Found: 52.17%C; 6.51%H; 10.85%N.

EXAMPLE 19

3-[4-[1-(3-Trifluoromethylphenyl)-4-piperazinyl]butyl]-4-thiazolidinone hydrochloride hemihydrate To a solution of 3-(4-bromobutyl)-4-thiazolidinone (3.0 g) and 1-(3-trifluoromethylphenyl)piperazine (2.91 g) in 100 ml of anhydrous $CH_3CN$ were added $K_2CO_3$ (3.5 g) and KI (200 mg). The mixture was heated to 80° with stirring under $N_2$.

After 18 hours the mixture was cooled to room temperature and filtered. The filtrate was concentrated in vacuo, taken up in EtOAc, filtered and concentrated. The residue was chromatographed on silica using EtOAc as the eluent, and fractions containing the product were combined and concentrated in vacuo.

The HCl salt of this amine was precipitated from $Et_2O$, dried and collected to provide 3.7458 g of product as a hemihydrate, mp 138°–140°.

ANALYSIS: Calculated for $C_{18}H_{24}N_3F_3OS.HCl.\frac{1}{2}H_2O$: 49.94%C; 6.05%H; 9.70%N. Found: 49.85%C; 6.07%H; 9.77%N.

EXAMPLE 20

3-[4-[1-(2-Methoxyphenyl)-4-piperazinyl]butyl]-1,4-dioxothiazolidine

A mixture of 3-(4-bromobutyl)-1,4-dioxothiazolidine (3.37 g), 1-(2-methoxyphenyl)piperazine (2.80 g), $K_2CO_3$ (4.60 g), NaI (190 mg) and $CH_3CN$ (150 ml) was heated at reflux (bath temperature 95° C.) for 24 h. TLC analysis (silica gel, 20% $MeOH/CH_2Cl_2$) showed the consumption of the starting sulfoxide and the presence of one major product with $R_f=0.43$. The mixture was cooled to room temperature, EtOAc (100 m) was added and the mixture was filtered. The filtrate was concentrated in vacuo to an oil which was filtered through silica gel using 20% $MeOH/CH_2Cl_2$ as the eluent. The fractions containing the material with $R_f=0.43$ were concentrated in vacuo to yield 4.83 g of a foam, which was dissolved in $MeOH/CH_2Cl_2$ and flash chromatographed (silica gel) to yield 3.28 g of a crude product. Rechromatography over silica gel using 50% MeOH/toluene as eluent yielded 2.98 g of an oil which solidified on standing. The solid was dissolved in 50% MeOH/EtOAc and filtered through silica gel. The filtrate containing the product was concentrated to approximately 5 ml and the oily liquid was seeded and left standing, yielding 0.91 g of a white solid, mp, 111°–113° C. The mother liquor was concentrated in vacuo to a solid which was recrystallized from $CH_2Cl_2/Et_2O$, yielding an additional 0.79 g of fine needles, mp, 111°–113° C.

ANALYSIS: Calculated for $C_{18}H_{27}N_3O_3S$: 59.15%C; 7.48%H; 11.50%N. Found: 59.02%C; 7.06%H; 11.49%N.

EXAMPLE 21

3-[4-[1-(4-Fluorophenyl)-4-piperazinyl]butyl]-1,4-dioxothiazolidine

To a solution of $NaIO_4$ (710 mg) in $H_2O$ (12 ml) was added a solution of 3-[4-[1-(4-fluorophenyl)-4-piperazinyl]butyl]-4-thiazolidinone 1, (1.02 g) in tetrahydrofuran (THF, 12 ml). The resultant mixture was stirred at room temperature for 18 h. TLC analysis (silica gel, 30% $MeOH/CHCl_3$) showed a major product with $R_f=0.33$ along with a material having the same $R_f$ as 1, namely 0.79. The mixture was filtered to remove the $NaIO_3$. The filtrate was concentrated in vacuo, poured into $H_2O$ (35 ml) and extracted with $CH_2Cl_2$ (4×20 ml). The combined extracts were washed with brine (50 ml), dried through $Na_2SO_4$ and concentrated to an oil. Flash chromatography over silica gel afforded 185 mg of material with $R_f$ identical to 1 and 0.520 g of an oil which solidified on standing.

A second run using $NaIO_4$ (1.41 g), $H_2O$ (13 ml), 1 (2.02 g) and THF (20 ml) was conducted in a similar manner yielding 0.910 g of product.

The combined products, 1.43 g, were dissolved in 50% MeOH/EtOAC and filtered through silica gel using 50% MeOH/EtOAc as eluent. The fractions containing the product were concentrated to approximately 8 ml, seeded, and left to deposit 1.02 g of a white crystalline material, mp, 118°–119.5° C.

ANALYSIS: Calculated for $C_{17}H_{24}N_3O_2FS$: 57.77%C; 6.84%H; 11.89%N. Found: 57.61%C; 6.83%H; 11.83%N.

EXAMPLE 22

3-[4-[1-(2-Methoxyphenyl)-4-piperazinyl]butyl]-2-Methyl-4-thiazolidinone

A suspension of 2-methyl-3-(4-bromobutyl)-4-thiazolidinone (3.0 g), 1-(2-methoxyphenyl)piperazine (2.3 g), anhydrous $K_2CO_3$ (3.5 g) and NaI (200 mg) in 100 ml of anhydrous $CH_3CN$ was heated to 80° under $N_2$. After 4 hours no starting material remained as judged by TLC. The mixture was cooled to room temperature, filtered and concentrated in vacuo. The residue was chromatographed on silica, using EtOAc as the eluent. This provided 2.18 g of product as a clear oil which solidified in vacuo (0.1 mmHg) overnight.

ANALYSIS: Calculated for $C_{19}H_{29}N_3O_2S$: 62.78%C; 8.04%H; 11.56%N. Found: 62.55%C; 7.94%H; 11.17%N.

EXAMPLE 23

3-[4-[1-(4-Fluorophenyl)-4-piperazinyl]butyl]-2-Methyl-4-thiazolidinone hydrochloride To a solution of 2-methyl-3-(4-bromobutyl)-4-thiazolidinone (3.0 g) and 1-(4-fluorophenyl)piperazine (2.15 g) in 100 ml of anhydrous $CH_3CN$ were added $K_2CO_3$ (3.5 g) and NaI (200 mg).

The mixture was heated to 80° with stirring under $N_2$. After 18 hours the mixture was cooled to room temperature and filtered. The filtrate was concentrated in vacuo, and the residue was taken up in EtOAc and chromatographed (silica, EtOAc eluent). The fractions containing the desired product were combined and concentrated.

The HCl salt was precipitated from $Et_2O$, collected and dried to provide 3.273 g of product as a white solid, mp 178°–182° (dec).

ANALYSIS: Calculated for $C_{18}H_{24}FN_3OS \cdot HCl$: 55.73%C; 7.01%H; 10.83%N. Found: 55.45%C; 6.90%H; 10.86%N.

EXAMPLE 24

3-[4-[1-(3-Chlorophenyl)-4-piperazinyl]butyl]-2-Methyl-4-thiazolidinone hydrochloride To a solution of 2-methyl-3-(4-bromobutyl)-4-thiazolidinone (4.0 g) and 1-(3-chlorophenyl)piperazine hydrochloride (3.69 g) in 100 ml of dry $CH_3CN$ were added $K_2CO_3$ (8.8 g) and NaI (200 mg). The mixture was heated to reflux with stirring under $N_2$.

After 18 hours the mixture was cooled to room temperature and filtered. The filtrate was concentrated in vacuo, taken up in EtOAc and chromatographed (silica, EtOAc as the eluent). The fractions containing the desired product were combined and concentrated. The HCl salt of the free amine was precipitated from $Et_2O$ and the excess HCl and $Et_2O$ were removed in vacuo to leave 5.176 g of product as a white solid, mp 180°–183° (dec.)

ANALYSIS: Calculated for $C_{18}H_{26}ClN_3OS \cdot HCl$: 53.46%C; 6.73%H; 10.39%N. Found: 53.27%C; 6.88%H; 10.27%N.

EXAMPLE 25

3-[4-[1-(2-Methoxyphenyl)-4-piperazinyl]butyl]-5-methyl-4-thiazolidinone oxalate A mixture of 3-(4-bromobutyl)-5-methyl-4-thiazolidinone (5.03 g), 1-(2-methoxyphenyl)piperazine (4.06 g), $K_2CO_3$ (7.28 g), NaI (190 mg) and $CH_3CN$ (100 mL) was refluxed (bath temperature 99° C.) for 48 h. TLC analysis (10% $EtOH/CH_2Cl_2$) showed the absence of starting bromide and formation of one major product, $R_f=0.48$. The reaction mixture was cooled to room temperature and filtered, the filtrate was concentrated in vacuo and passed through silica gel to yield 6.06 g of an amber oil. Chromatography of the crude product, followed by treatment with ethereal HCl yielded 5.45 g of a salt. Attempts to recrystallize the crude salt failed, so it was freebased utilizing 5% $NaHCO_3$ yielding, after an EtOAc extraction, 3.82 g of an oil. The oil was chromatographed (silica gel, 10% $EtOH/CH_2Cl_2$) yielding 2.2 g of an oil which solidified on standing. The solid was rechromatographed (silica gel, 10% $EtOH/CH_2Cl_2$) and dissolved in $Et_2O$ (200 ml), and its oxalate salt was precipitated by the addition of a saturated solution of oxalic acid in $Et_2O$. The oxalate was dried in vacuo and recrystallized from EtOAc to yield fine white needles, mp 129°–131° C.

ANALYSIS: Calculated for $C_{19}H_{29}N_3O_2S \cdot C_2H_2O_4$: 55.61%C; 6.89%H; 9.26%N. Found: 55.56%C; 6.86%H; 9.33%N.

EXAMPLE 26

2,2-Dimethyl-3-[4-[1-(3-methylphenyl)-4-piperazinyl]-butyl]-4-thiazolidinone dihydrochloride A mixture of 2,2-dimethyl-3-(4-bromobutyl)-4-thiazolidinone (4.01 g), 1-(3-methylphenyl)piperazine (3.17 g), $K_2CO_3$ (5.30 g), NaI (230 mg) and $CH_3CN$ (180 mL) was heated at reflux (oil bath temperature; 100° C.) for 20 h. TLC analysis (silica gel, 7.5% EtOH/$CH_2Cl_2$ showed one major product, $R_f$=0.53, and a trace of starting bromide, $R_f$=0.70. The reaction mixture was cooled to room temperature, EtOAc (100 mL) was added and the mixture filtered. The filtrate was concentrated in vacuo to an oil which was triturated with EtOAc (150 mL). The mixture was filtered and the filtrate concentrated in vacuo to an oil. HPLC of the crude oil (Waters Prep 500 silica gel, 8% MeOH/EtOAc) yielded 5.42 g of an oil, $R_f$=0.53. The hydrochloride salt of this amine was precipitated by the addition of HCl/$Et_2O$ to a solution of the base in 600 ml of ether until pH=2 to give 5.30 g of a white powder. Recrystallization from EtOH yielded 2.91 g of white crystals, mp 204° C. (dec).

ANALYSIS: Calculated for $C_{20}H_{31}N_3OS \cdot 2HCl$: 55.29%C; 7.66%H; 9.67%N; 16.32%Cl. Found: 55.41%C; 8.07%H; 9.78%N; 16.65%Cl.

EXAMPLE 27

2,2-Dimethyl-3-[4-[1-(2-methoxyphenyl)-4-piperazinyl]butyl]-4-thiazolidinone hydrochloride hydrate To a solution of 2,2-dimethyl-3-(4-chlorobutyl)-4-thiazolidinone (3.26 g) and 1-(2-methoxyphenyl)piperazine (2.8 g) in 100 ml of anhydrous $CH_3CN$ were added anhydrous $K_2CO_3$ (4.5 g) and NaI (200 mg). The mixture was heated with stirring to 80° under $N_2$.

After 18 hours the mixture was cooled to room temperature and filtered, concentrated in vacuo, taken up in EtOAc and again filtered. The EtOAc was removed in vacuo and the residue chromatographed on silica using EtOAc as the eluent to provide 4.2 g of amine.

The HCl salt was precipitated from $Et_2O$ and dried in vacuo to provide a monohydrate, homogeneous by TLC, mp 189°–192° C. The yield was 4.465 g.

ANALYSIS: Calculated for $C_{20}H_{31}N_3O_2S \cdot HCl \cdot H_2O$: 55.60%C; 7.93%H; 9.72%N. Found: 55.28%C; 7.61%H; 9.53%N.

Karl Fisher Titration: Calculated: 4.17%. Found: 4.36%.

EXAMPLE 28

2,2-Dimethyl-3-[4-[1-(3-chlorophenyl)-4-piperazinyl]-butyl]-4-thiazolidinone dihydrochloride A mixture of 2,2-dimethyl-3-(4-bromobutyl)-4-thiazolidinone (4.02 g), 1-(3-chlorophenyl)piperazine hydrochloride (3.85 g), $K_2CO_3$ (6.84 g), NaI (200 mg) and $CH_3CN$ (160 mL) was refluxed (bath temperature 95° C.) under $N_2$ for 48 h. TLC analysis (silica gel, 7.5% EtOH/$CH_2Cl_2$) showed one major product, $R_f$=0.33 and the absence of starting thiazolidinone. The mixture was cooled to room temperature, EtOAc (100 ml) was added, and the mixture filtered. The filtrate was concentrated in vacuo to an oil which was redissolved in EtOAc causing a white solid to precipitate. The mixture was filtered and the filtrate concentrated in vacuo to an oil. Purification of the crude product by HPLC (Waters Prep 500 A, 5% EtOH/EtOAc) afforded 4.35 g of oil. The oil was dissolved in $Et_2O$ (600 mL) and the solution acidified to pH=2 (hydrion paper) with an HCl/$Et_2O$ solution, and the precipitated salt (3.7 g) was recrystallized from EtOH to yield 2.10 g of a crystalline solid, mp 205°–207° C.

ANALYSIS: Calculated for $C_{19}H_{28}N_3ClOS \cdot 2HCl$: 50.16%C; 6.65%H; 9.24%N. Found: 50.23%C; 6.57%H; 9.19%N.

EXAMPLE 29

2,2-Dimethyl-3-[4-[1-(3-trifluoromethyl)-4-piperazinyl]-butyl]-4-thiazolidinone dihydrochloride A mixture of 2,2-dimethyl-3-(4-bromobutyl)-4-thiazolidinone (4.06 g), 1-(3-trifluoromethylphenyl)piperazine (4.07 g), $K_2CO_3$ (5.11 g), NaI (200 mg) and $CH_3CN$ (160 mL) under $N_2$ was heated at reflux for 24 h. The reaction mixture was cooled to room temperature and filtered, and the filtrate concentrated in vacuo to an amber oil. The oil was triturated with EtOAc and the mixture was filtered. The filtrate was concentrated in vacuo to an oily residue which was chromatographed by HPLC (silica gel, 5% EtOH/EtOAc) to give 4.85 g of product which solidified on cooling. The solid was dissolved in $Et_2O$ (500 mL) and its HCl salt precipitated by addition of HCl/$Et_2O$. It was dried in vacuo and recrystallized from isopropanol to yield white crystals, mp 184° C. (dec).

ANALYSIS: Calculated for $C_{20}H_{30}F_3Cl_2N_3OS \cdot 2HCl$: 49.18%C; 6.19%H; 8.60%N. Found: 49.24%C; 6.52%H; 8.84%N.

EXAMPLE 30

2,2-Dimethyl-3-[4-[1-(3-methylmercaptophenyl)-4-piperazinyl]butyl]-4-thiazolidinone dihydrochloride A mixture of 2,2-dimethyl-3-(4-bromobutyl)-4-thiazolidinone (4.17 g), 1-(3-methylmercaptophenyl)piperazine (3.92 g), $K_2CO_3$ (5.42 g), NaI (240 mg) and $CH_3CN$ (180 mL) was heated to reflux (bath temperature 100° C.) under $N_2$ for 24 h. TLC analysis (silica gel, 5% EtOH/EtOAc) showed the absence of starting bromide and the presence of one major product with $R_f$=0.23. The reaction mixture was cooled to room temperature, EtOAc (100 mL) was added, and the mixture filtered. The filtrate was concentrated in vacuo to an oil which was chromatographed by HPLC (silica gel, 8% MeOH/EtOAc) to give 5.60 g of a yellow oil. The oil was dissolved in $Et_2O$ (450 mL) and the HCl salt of this amine was precipitated by the addition of an HCl/$Et_2O$ solution, yielding 6.26 g of a white solid. Recrystallization of the crude product from EtOH (250 mL) and HCl/$Et_2O$ solution (2 mL) afforded 3.79 g of fine crystals, mp 202° C. (dec).

ANALYSIS: Calculated for $C_{20}H_{31}N_3OS_2 \cdot 2HCl$: 51.49%C; 7.13%H; 9.01%N. Found: 51.32%C; 7.42%H; 8.86%N.

EXAMPLE 31

5,5-Dimethyl-3-[4-[1-(2-methoxyphenyl)-4-piperazinyl]butyl]-4-thiazolidinone dihydrochloride A mixture of 5,5-dimethyl-3-(4-bromobutyl)-4-thiazolidinone (4.25 g), 1-(2-methoxyphenyl)piperazine hydrochloride (4.38 g), K$_2$CO$_3$ (8.8 g), NaI (300 mg) and acetonitrile (200 mL) was heated at 110° C. (bath temperature) under nitrogen. After 25 hours, TLC analysis (silica gel, 10% methanol/ethyl acetate) showed the absence of starting bromide and a major product, R$_f$=0.20. The reaction mixture was cooled to room temperature, ethyl acetate (150 mL) was added, and the mixture filtered. The filtrate was concentrated in vacuo to an oil which was redissolved in ethyl acetate causing a solid to precipitate. The mixture was filtered and the filtrate concentrated to 6.01 g of an oily residue which was chromatographed (Waters Prep 500, one silica gel column, 10% methanol/ethyl acetate) to give 3.02 g of an oil. Trituration of the oil with diethyl ether (300 mL) deposited a fluffy white solid which was removed by filtration. The filtrate was acidified with an HCl/diethyl ether solution to pH=1 and the resulting salt (3.25 g) was collected as a white solid. After one recrystallization from EtOH/ethyl acetate the salt was freebased to give 2.45 g of an oil which was dissolved in diethyl ether. The solution was filtered and the filtrate acidified with an HCl/diethyl ether solution again to yield 2.60 g of a salt. Recrystallization from EtOH/ether yielded 2.29 g of a white solid, mp 213°–218° (dec.).

ANALYSIS: Calculated for C$_{20}$H$_{31}$N$_3$O$_2$S.2HCl: 53.32%C; 7.38%H; 9.33%H; 15.74%Cl. Found: 53.40%C; 7.46%H; 9.34%H; 15.76%Cl.

EXAMPLE 32

5,5-Dimethyl-3-[4-[1-(3-trifluoromethylphenyl)-4-piperazinyl]butyl]-4-thiazolidinone hydrochloride A mixture of 5,5-dimethyl-3-(4-bromobutyl)-4-thiazolidinone (4.00 g), 1-(3-trifluoromethylphenyl)piperazine (4.15 g), K$_2$CO$_3$ (6.22 g), NaI (220 mg) and CH$_3$CN (120 mL) was refluxed (oil bath temperature=97° C.) under N$_2$ for 20 h. TLC analysis (silica gel, 10% MeOH/EtOAc) of the reaction mixture showed one major product, R$_f$=0.49, and the absence of starting bromide. The mixture was cooled to room temperature, EtOAc (150 mL) was added, and the mixture filtered. The filtrate was concentrated in vacuo to a yellow oil. The oil was triturated with EtOAc (200 mL) and filtered, and the filtrate concentrated in vacuo to an oil. The crude oily product was chromatographed (Waters Prep 500, 2 silica gel columns, 5% MeOH/EtOAc) to give 4.2 g of a clear oil. The HCl salt of this amine was precipitated by the addition of a diethyl ether/HCl solution until pH=2 (hydrion paper). The resultant salt was collected, dried and recrystallized from ethanol/ethyl acetate to afford 2.85 g of crystals, mp 169°–171° C.

ANALYSIS: Calculated for C$_{20}$H$_{28}$F$_3$N$_3$OS.HCl: 53.15%C; 6.47%H; 7.84%N; 9.30%Cl. Found: 53.10%C; 6.61%H; 8.09%N; 9.29%Cl.

EXAMPLE 33

5-Phenyl-3-[4-[1-(3-trifluoromethylphenyl)-4-piperazinyl]butyl]-4-thiazolidinone oxalate A mixture of 3-(4-bromobutyl)-5-phenyl-4-thiazolidinone (4.67 g), 1-(3-trifluoromethylphenyl)piperazine (3.76 g), K$_2$CO$_3$ (5.15 g), NaI (300 mg) and CH$_3$CN (150 mL) was heated at reflux (bath temperature 95° C.) under N$_2$. After 17 hours, TLC analysis (silica gel, 5% MeOH/EtOAc) showed the absence of starting bromide and presence of one major product with an R$_f$=0.33. The mixture was cooled to room temperature, EtOAc (100 mL) was added, and the mixture filtered. The filtrate was concentrated in vacuo to an oil which was triturated with EtOAc. The mixture was filtered and the filtrate concentrated again in vacuo to 7.59 g of an oil. The crude product was chromatographed (Waters Prep 500, 2 columns, silica gel, 5% MeOH/EtOAc) to give 6.42 g of an oil, and from this 4.47 g of the oxalate salt of this amine was prepared. The solid was recrystallized from EtOH/EtOAc giving 3.65 g of fine white crystals, mp 140°–142° C.

ANALYSIS: Calculated for C$_{24}$H$_{28}$F$_3$N$_3$OS.C$_2$H$_2$O$_4$: 56.41%C; 5.46%H; 7.59%N. Found: 56.31%C; 5.56%H; 7.53%N.

EXAMPLE 34

2-Methyl-3-[4-[1-(2-pyrimidyl)-4-piperazinyl]butyl]-4-thiazolidinone maleate

To a stirred solution of 3-(4-bromobutyl)-2-methyl-4-thiazolidinone (3.0 g) and 1-(2-pyrimidinyl)piperazine dihydrochloride (2.83 g) in 100 ml of dry CH$_3$CN were added K$_2$CO$_3$ (6.6 g) and NaI (200 mg). The mixture was heated to reflux under N$_2$.

After 18 hours, the mixture was cooled to room temperature and filtered. The filtrate was concentrated in vacuo, taken up in EtOAc and chromatographed (silica, 10:90 CH$_3$OH/EtOAc). The fractions containing the desired product were combined and concentrated.

The maleate salt was precipitated from Et$_2$O, collected and dried to provide 3.18 g of product as a white solid, mp 155°–157° C., homogeneous by TLC (silica, 10:88:2 CH$_2$OH/EtOAc/Et$_3$N, R$_f$=0.26).

ANALYSIS: Calculated for C$_{16}$H$_{25}$N$_5$OS.C$_4$H$_4$O$_4$: 53.20%C; 6.47%H; 15.51%N. Found: 53.00%C; 6.65%H; 15.43%N.

EXAMPLE 35

3-[4-[1-(1,2-Benzisothiazol-3-yl)-4-piperazinyl]butyl]-4-thiazolidinone hydrochloride A mixture of 3-(4-bromobutyl)-4-thiazolidinone (3.50 g), 1-(1,2-benzisothiazol-3-yl)piperazine (3.87 g), K$_2$CO$_3$ (6.09 g), NaI (200 mg) and acetonitrile (130 mL) was heated at reflux (bath temperature 95° C.) under nitrogen. After 30 hours, TLC analysis (silica gel, 10% MeOH/EtOAc) showed the absence of the starting bromide and the presence of a major product (R$_f$≅0.21) and a minor product (R$_f$≅0.30). The reaction mixture was cooled to room temperature, ethyl acetate (150 mL) was added and the mixture was filtered. The filtrate was concentrated in vacuo to a brown oil which was triturated with EtOAc. The mixture was filtered and the filtrate, after concentration in vacuo, was chromatographed (Waters Prep 500, silica gel, 15% MeOH/EtOAc) to give 2.75 g of a yellowish oil.

The chromatographed free base (3.88 g) was dissolved in ethyl acetate/diethyl ether, the resulting mixture was filtered in order to remove a fluffy insoluble material, and the filtrate was acidified with an HCl/diethyl ether solution until pH=1 (hydrion paper). The resultant solid was collected and dried at 55° C./3.0 mmHg yielding 3.1 g of a beige solid, mp 219°–222° C. Recrystallization from EtOH (165 mL) yielded after drying (78° C./0.30 mmHg) 2.65 g of amber crystals, mp 220°–225° C.

ANALYSIS: Calculated for C$_{18}$H$_{24}$N$_4$OS$_2$.HCl: 52.35%C; 6.10%H; 13.57%N; 8.58%Cl. Found: 52.10%C; 6.03%H; 13.41%N; 8.85%Cl.

EXAMPLE 36

3-[4-[1-(1,2-Benzisothiazol-3-yl)-4-piperazinyl]butyl]-5,5-dimethyl-4-thiazolidinone hydrochloride A mixture of 3-(4-bromobutyl)-5,5-dimethyl-4-thiazolidinone (3.50 g), 1-(1,2-benzisothiazol-3-yl)piperazine hydrochloride (3.70 g), $K_2CO_3$ (6.34 g), NaI (330 mg) and acetonitrile (175 mL) was heated at 95° C. (bath temperature) under nitrogen. After 21 hours, TLC analysis (silica gel, 5% MeOH/$CH_2Cl_2$) showed the absence of starting bromide and the presence of a major product, $R_f=0.33$. The reaction mixture was cooled to room temperature, ethyl acetate (150 mL) was added, and the mixture filtered. The filtrate was concentrated in vacuo to an oil which was triturated with ethyl acetate. The mixture was filtered again and the filtrate, after concentration, was chromatographed (Waters Prep 500, one silica gel column, 3% MeOH/$CH_2Cl_2$) to give 3.48 g of a viscous oil. The oil was dissolved in diethyl ether (500 mL), the solution filtered to remove a fluffy solid, and the filtrate acidified to pH=1 (hydrion paper) with an HCl/diethyl ether solution. The resultant salt (3.23 g) was recrystallized from ethanol/ethyl acetate yielding 2.29 g of white needles, mp 222°–227° C.

ANALYSIS: Calculated for $C_{20}H_{28}N_4OS_2 \cdot HCl$: 54.46%C; 6.63%H; 12.70%N; 8.04%Cl. Found: 53.93%C; 6.73%H; 12.58%N; 8.57%Cl.

EXAMPLE 37

3-[4-[1-(2-Benzothiazolyl)-4-piperazinyl]butyl]-5,5-dimethyl-4-thiazolidinone A mixture of 3-(4-bromobutyl)-5,5-dimethyl-4-thiazolidinone (3.42 g), 1-(2-benzothiazolyl)piperazine (3.10 g), $K_2CO_3$ (6.19 g), NaI (250 mg) and acetonitrile was heated at 65° C. (bath temperature) under nitrogen. After 19 hours, TLC analysis (5% methanol/methylene chloride) showed the absence of starting bromide and the presence of a major product, $R_f=0.29$. The reaction mixture was cooled to room temperature, ethyl acetate (100 ml) was added and the mixture filtered. The filtrate was concentrated in vacuo to a solid which was redissolved in hot ethyl acetate causing a solid to precipitate. The mixture was filtered and the filtrate concentrated in vacuo to an off-white solid. Chromatography of the crude product by HPLC (Waters Prep 500, one silica gel column, 5% methanol/methylene chloride) yielded 4.05 g of a solid, mp 99.5°–100.5° C. It was recrystallized from methylene chloride/hexane to give 2.83 g of fine needles, mp 101°–102° C.

ANALYSIS: Calculated for $C_{20}H_{28}N_4OS_2$: 59.37%C; 6.98%H; 13.85%N. Found: 59.29%C; 7.06%H; 14.01%N.

EXAMPLE 38

3-[4-[1-(2-Quinolinyl)-4-piperazinyl]butyl]-4-thiazolidinone

A mixture of 3-(4-bromobutyl)-4-thiazolidinone (4.00 g), 1-(2-quinolinyl)piperazine (3.94 g), $K_2CO_3$ (6.97 g), NaI (230 mg) and acetonitrile (150 mL) was heated at 80° C. (bath temperature) under nitrogen. After 19 hours, TLC analysis (silica gel, 13% MeOH/EtOAc) showed the absence of starting bromide and the presence of one major product, $R_f=0.19$. The reaction mixture was cooled to room temperature, ethyl acetate (100 mL) was added, and the mixture was filtered. The filtrate was concentrated in vacuo to a solid and triturated with EtOAc. The mixture was filtered again to remove insoluble materials and the filtrate concentrated in vacuo to 6.32 g of beige solid. Chromatography of the crude product by HPLC (Waters Prep 500, one silica gel column 8% MeOH/$CH_2Cl_2$) yielded 5.67 g of a solid, mp 105°–107° C. It was recrystallized from ethyl acetate/cyclohexane to give 3.62 g of off-white crystals, mp 106°–107.5° C.

ANALYSIS: Calculated for $C_{20}H_{26}N_4OS$: 64.83%C; 7.07%H; 15.12%N. Found: 64.78%C; 7.07%H; 15.18%N.

EXAMPLE 39

5,5-Dimethyl-3-[4-[1-(2-quinolinyl)-4-piperazinyl]butyl]-4-thiazolidinone

A mixture of 5,5-dimethyl-3-(4-bromobutyl)-4-thiazolidinone (4.20 g), 1-(2-quinolinyl)piperazine (3.70 g), $K_2CO_3$ (6.55 g), NaI (200 mg) and acetonitrile (150 mL) was heated at reflux (bath temperature 95° C.) under $N_2$ for 20 h. TLC analysis (silica gel, 10% MeOH/EtOAc) showed the absence of starting bromide and the formation of a major product, $R_f=0.31$. The reaction mixture was cooled to room temperature and left standing for 44 h. To this was added ethyl acetate (100 ml) and the resultant mixture was filtered. The filtrate was concentrated in vacuo to an oily solid which was redissolved in ethyl acetate (200 mL) causing a white solid to precipitate. The mixture was gravity filtered and the filtrate concentrated to an off-white solid (6.86 g). Chromatography of the crude product (Waters Prep 500, 1 silica gel column, 10% MeOH/EtOAc) yielded 4.22 g of a white solid ($R_f=0.26$), mp 107°–111° C. It was recrystallized from ethyl acetate/hexane (1:2) to yield 2.83 g of white crystals, mp 110.5°–111.5° C.

ANALYSIS: Calculated for $C_{22}H_{30}N_4OS$: 66.29%C; 7.59%H; 14.06%N. Found: 66.26%C; 7.61%H; 13.95%N.

EXAMPLE 40

3-[4-[1-(1,2-Benzisothiazol-3-yl)-4-piperazinyl]butyl]-2,2-dimethyl-4-thiazolidinone hydrochloride A mixture of 3-(4-bromobutyl)-4-thiazolidinone (4.00 g), 1-(1,2-benzisothiazol-3-yl)piperazine (3.62 g), $K_2CO_3$ (7.25 g), NaI (400 mg) and $CH_3CN$ (180 mL) was heated at 80° C. under nitrogen. After 20 h, TLC analysis (silica gel, 5% MeOH/$CH_2Cl_2$) showed the absence of starting bromide and the presence of a major product, $R_f=0.40$. The mixture was cooled to room temperature, EtOAc (100 mL) was added, and the mixture filtered. The filtrate was concentrated in vacuo to an oil which was dissolved in EtOAc (150 mL) causing a small amount of solid to precipitate. The mixture was filtered again and the filtrate concentrated to a yellowish brown oil. The oil was chromatographed (Waters Prep 500, 1 silica gel column, 4% MeOH/$CH_2Cl_2$) to yield 5.10 g of a yellowish solid.

The solid (5.00 g) was dissolved in EtOAc (100 mL)/$Et_2O$ (500 mL) and the resultant cloudy solution was filtered to remove a small amount of brown solid. The filtrate was acidified with an HCl/$Et_2O$ solution until pH=2. The resultant salt was collected and dried to give 5.15 g of an off-white powder, mp 211°–214° C. A 4.00 g sample of the salt was recrystallized from EtOH/ethyl acetate to yield 2.92 g of white needles, mp 213°–216° C.

ANALYSIS: Calculated for $C_{20}H_{28}N_4OS_2 \cdot HCl$: 54.46%C; 6.63%H; 12.70%N; 8.04%Cl. Found: 54.16%C; 6.66%H; 12.58%N; 8.10%Cl.

EXAMPLE 41

3-[4-[1-(2-Benzothiazolyl)-4-piperazinyl]butyl]-4-thiazolidinone

A mixture of 3-(4-bromobutyl)-4-thiazolidinone (4.00 g), 1-(2-benzothiazolyl)piperazine (4.05 g), $K_2CO_3$ (7.01 g), NaI (250 mg) and acetonitrile (160 mL) was heated at 93° (bath temperature) under nitrogen. After 19 h, TLC analysis (silica gel, 5% methanol/methylene chloride) showed the absence of starting bromide and the presence of a major product, $R_f=0.26$. The reaction mixture was cooled to room temperature, ethyl acetate (100 mL) was added, and the mixture filtered. The filtrate was concentrated in vacuo to a solid which was redissolved in ethyl acetate causing a white solid to precipitate. The mixture was filtered again and the filtrate concentrated in vacuo to 6.43 g of an off-white solid. Chromatography of the crude product by HPLC (Waters Prep 500, 1 silica gel column, 5% methanol/methylene chloride) yielded 5.44 g of an off-white solid. A sample of the solid (3.08 g) was recrystallized from methylene chloride (15 mL)/hexanes (85 mL) yielding 2.28 g of a crystalline solid, mp 111°-112° C.

ANALYSIS: Calculated for $C_{18}H_{24}N_4OS_2$: 57.42%C; 6.42%H; 14.88%N. Found: 57.36%C; 6.38%H; 14.83%N.

EXAMPLE 42

3-[4-[1-(3-Isoquinolinyl)-4-piperazinyl]butyl]-5,5-dimethyl-4-thiazolidinone

A mixture of 3-(4-bromobutyl)-4-thiazolidinone (4.00 g), 1-(3-isoquinolinyl)piperazine (3.53 g), $K_2CO_3$ (6.22 g), NaI (300 mg) and acetonitrile (190 mL) was heated at 75° C. (bath temperature) under $N_2$. After 16 h, TLC analysis (silica gel, 40% EtOAc/hexane) showed the absence of starting bromide and a major product at $R_f=0.22$ (silica gel, 5% $MeOH/CH_2Cl_2$). The reaction mixture was cooled to ambient temperature and filtered, the inorganic solid was washed with hot ethyl acetate, and the wash was combined with the above filtrate and concentrated in vacuo to a green solid. The solid was triturated with hot ethyl acetate (300 mL) and the mixture filtered. The filtrate was concentrated in vacuo to a solid which was chromatographed (Waters Prep 500, 1 silica gel column, 5% $MeOH/CH_2Cl_2$) to yield 5.10 g of a green solid. The solid was recrystallized from methylene chloride/hexanes to give 2.99 g of light green crystals, mp 145°-146.5° C.

ANALYSIS: Calculated for $C_{22}H_{30}N_4OS$: 66.29%C; 7.59%H; 14.06%N. Found: 66.45%C; 7.60%H; 14.00%N.

EXAMPLE 43

3-(4-Bromobutyl)-2,2,5,5-tetramethyl-4-thiazolidinone

To a −75° C. solution of 3-(4-bromobutyl)-2,2-dimethyl-4-thiazolidinone (13.18 g), iodomethane (22.83 g) and THF (30 ml) was added a −75° C. solution of lithium bis(trimethylsilyl)amide (0.100 mol) in THF (110 ml) over a period of 12 minutes. The resulting solution was stirred at −75° C. for 25 minutes, removed from the cold bath and acidified with 1N HCl (250 ml). The aqueous mixture was extracted with diethylether (3×125 ml). The combined extracts were washed with brine (150 ml), dried (anhydrous $Na_2SO_4$) and concentrated under reduced pressure to give 16.86 g of liquid. Column chromatography of the liquid using silica gel (about 600 g) and elution with 30% ethyl acetate/hexanes afforded 12.50 g of oil.

Molecular distillation of 2.5 g of the oil (0.10 mmHg/92°-100° C. bath temperature) yielded 2.1 g of a colorless oil which solidified on cooling, m.p. 30°-31° C.

ANALYSIS: Calculated for $C_{11}H_{20}BrNOS$: 44.90%C; 6.85%H; 4.76%N. Found: 44.65%C; 6.92%H; 4.67%N.

EXAMPLE 44

2-Methyl-3-(4-bromobutyl)-1-thia-3-aza[4.4]nonan-4-one

To a solution prepared from 2-methyl-3-(4-bromobutyl)-4-thiazolidinone (8.00 g), 1,4-diiodobutane (11 ml) and THF (75 ml) and maintained at −60° C. was added dropwise under nitrogen a solution of lithium bis(trimethylsilyl)amide (0.066 mole) in THF (66 ml) during which the temperature was maintained below −54° C. The addition was complete within 20 minutes. The reaction mixture was stirred for additional 30 minutes, the cold bath was removed, the mixture was warmed to 5° C. and it was quenched with 200 ml of 0.66N HCl solution. The resultant mixture was placed under vacuum to remove the THF and extracted with ether (3×100 ml). The ether extract was washed successively with water (150 ml) and brine (150 ml) and thereafter dried ($Na_2SO_4$) and concentrated to yield a viscous liquid. The oil was chromatographed on silica gel (500 g) using 30-50% ethyl acetate/hexane as eluent to obtain 6.38 g of liquid.

EXAMPLE 45

3-(4-Bromobutyl)-1-thia-3-azaspiro[5.4]decan-4-one

To a solution of 3-(4-bromobutyl)-4-thiazolidinone (25 g) in THF (350 ml) cooled to −60° C. was added 1,5-diiodopentane (100 g), and the resultant slurry was cooled to −65° C. A solution of lithium bis(trimethylsilyl)amide (0.220 mole) in hexanes (220 ml) was added dropwise, during which the internal temperature was maintained at or below −55° C. The addition was complete within 30 minutes. The mixture was stirred for additional 15 minutes at the same temperature and thereafter warmed to 0° C. with the aid of an ice bath. The mixture was stirred for additional 20 minutes and thereafter quenched with 500 ml of 0.5N HCl solution. The resultant mixture was placed under vacuum to remove some of the THF and thereafter extracted with ether (350 ml, 2×250 ml). The combined extracts were washed successively with water (400 ml) and brine (400 ml), dried with $Na_2SO_4$ and concentrated to a liquid. The liquid was chromatographed (2 silica gel columns) using 20-60% ethyl acetate/hexane as an eluent to obtain about 20.5 g of solid product.

EXAMPLE 46

3-(4-Bromobutyl)-5-(2-hydroxyisopropyl)-4-thiazolidinone

To a solution of 3-(4-bromobutyl)-4-thiazolidinone (10.0 g) in tetrahydrofuran (200 ml) cooled to −78° C. under nitrogen was added rapidly a solution of lithium bis(trimethylsilyl)amide (0.044 mol) in tetrahydrofuran (44 ml) followed immediately by acetone (10 ml). The resulting solution was stirred at −78° C. for 20 minutes, the cold bath was removed and 0.5N HCl (250 ml) was added. The aqueous mixture was placed under reduced pressure to remove some of the tetrahydrofuran. The resulting mixture was extracted with ether (3×125 ml). The combined extracts were washed with brine (200 ml), dried ($Na_2SO_4$) and concentrated to a viscous liquid. The liquid was chromatographed on silica gel (400 g) eluting with 50–100% ethyl acetate/hexanes to afford 8.96 g of oil. The oil was dried at 0.2 mmHg for 48 hours.

ANALYSIS: Calculated for $C_{10}H_{18}BrNO_2S$: 40.55%C; 6.12%H; 4.73%N. Found: 40.20%C; 6.17%H; 4.67%N.

EXAMPLE 47

3-(4-Bromobutyl)-5-(2-fluoroisopropyl)-4-thiazolidinone

To a −67° C. solution of dimethylaminosulfur trifluoride (3.15 g) and dichloromethane (100 ml) under nitrogen was added a solution of 3-(4-bromobutyl)-5-(2-hydroxyisopropyl)-4-thiazolidinone (7.01 g) and dichloromethane (30 ml) dropwise over a period of 35 minutes. The resulting solution was allowed to warm to ambient temperature over a period of 80 minutes. Cold water (75 ml) was added and the layers were separated. The organic layer was washed successively with water (75 ml) and brine (100 ml), dried ($NaSO_4$) and concentrated to a liquid. The liquid was purified by chromatography on silica gel (350 g) eluting with 40–60% ethyl acetate/hexanes to give 6.01 g oil. A 2.07 g sample of oil was distilled using a molecular still (120° C./0.20 mmHg) to give 1.75 g of a clear liquid.

ANALYSIS: Calculated for $C_{10}H_{17}BrFNOS$: 40.28%C; 5.75%H; 4.70%N. Found: 40.39%C; 5.82%H; 4.56%N.

EXAMPLE 48

3-[4-[1-(2-Methylphenyl)-4-piperazinyl]butyl]-5,5-dimethyl-4-thiazolidinone hydrochloride A mixture of 3-(4-bromobutyl)-5,5-dimethyl-4-thiazolidinone (4.00 g), 1-(2-methylphenyl)-piperazine (3.87 g), $K_2CO_3$ (8.31 g), NaI (290 mg) and acetonitrile (175 ml) was heated at 75° C. (bath temperature) under nitrogen. After 16 hours, TLC analysis (silica gel, 5% $MeOH/CH_2Cl_2$) showed absence of the starting bromide and presence of a major product, $R_f=0.24$. The reaction mixture was cooled to room temperature, ethyl acetate (150 ml) was added, and the mixture filtered. The filtrate was concentrated in vacuo to an oil which was dissolved into ethyl acetate causing a solid to precipitate. The mixture was filtered and the filtrate concentrated in vacuo to 6.35 g of an oil. The oil was chromatographed (5% $MeOH/CH_2Cl_2$, one silica gel column) to obtain 4.91 g of a solid. The solid was dissolved in diethylether (550 ml), the solution filtered to remove a trace of insoluble material, and the filtrate acidified to pH=1 with a HCl/diethylether solution. The resulting salt was collected and dried to give 4.83 g of powder. The powder was recrystallized twice from ethanol-/ethyl acetate to yield 2.14 g of crystals, m.p. 230°–235° C.

ANALYSIS: Calculated for $C_{20}H_{31}N_3OS.HCl$: 60.35%C; 8.11%H; 10.56%N; 8.91%Cl. Found: 60.27%C; 8.27%H; 10.52%N; 9.02%Cl.

EXAMPLE 49

3-[4-[1-(2,3-Dimethylphenyl)-4-piperazinyl]butyl]-5,5-dimethyl-4-thiazolidinone hydrochloride A mixture of 1-(2,3-dimethylphenyl)piperazine (3.56 g), 3-(4-bromobutyl)-5,5-dimethyl-4-thiazolidinone (3.80 g), $K_2CO_3$ (7.90 g), NaI (380 mg) and $CH_3CN$ (210 ml) was heated at 80° C. (oil bath temperature) under nitrogen. After 17 hours, the mixture was cooled to ambient temperature, EtOAc (125 ml) was added, and the inorganics filtered. The filtrate was concentrated under reduced pressure to give 5.59 g of viscous liquid. The crude product was purified by preparative HPLC on silica gel eluting with 5% $MeOH/CH_2Cl_2$ to yield 3.80 g of solid, m.p. 100°–104° C., $R_f=0.43$. The HCl salt of this amine was prepared to afford 3.58 g of powder. Recrystallization of the salt from $CH_2Cl_2/EtOAc$ gave 2.43 g of fine needles, m.p. 248°–256° C.

ANALYSIS: Calculated for $C_{21}H_{33}N_3OS.HCl$: 61.21%C; 8.32%H; 10.20%N; 8.60%Cl. Found: 60.85%C; 8.33%H; 10.12%N; 8.91%Cl.

EXAMPLE 50

3-[4-[1-(3-Phenyl-1H-indolyl)-4-piperazinyl]butyl]-5,5-dimethyl-4-thiazolidinone dihydrochloride A mixture of 3-(4-bromobutyl)-4-thiazolidinone (2.3 g), 1-phenyl-3-piperazino-1H-indole (2.17 g), $K_2CO_3$ (2.2 g), NaI (200 mg) and 150 ml anhydrous $CH_3CN$ was heated to 80° C. with stirring under $N_2$. After 18 hours no starting material remained as judged by TLC. The mixture was cooled to room temperature, filtered and the filtrate concentrated in vacuo. The residue was chromatographed on silica using EtOAc as an eluent. The fractions containing the desired product were combined, concentrated and taken up in $Et_2O$. The HCl salt of the amine was precipitated by the addition of HCl in $Et_2O$, and recrystallized from $Et_2O/CH_2Cl_2$ to provide 1.349 g of product as bis-salt, m.p. 205°–208° C., homogeneous by TLC.

ANALYSIS: Calculated for $C_{27}H_{34}N_4OS.2HCl$: 60.55%C; 6.78%H; 10.46%N. Found: 60.94%C; 6.41%H; 10.40%N.

EXAMPLE 51

3-[4-[1-[1-(4-Fluorophenyl)-1H-indol-3-yl]-4-piperazinyl]butyl]-5,5-dimethyl-4-thiazolidinone dihydrochloride A mixture of 3-(4-bromobutyl)-4-thiazolidinone (3.2 g), 1-(4-fluorophenyl)-3-piperazino-1H-indole (3.6 g), $K_2CO_3$ (3.4 g), NaI (200 mg) and 150 ml anhydrous $CH_3CN$ was heated to 80° C. with stirring under $N_2$. After 18 hours no starting material remained as judged by TLC. The mixture was cooled to room temperature and filtered, and the filtrate concentrated in vacuo. The residue was chromatographed on silica using EtOAc as an eluent. The fractions containing the desired product were combined and concentrated in vacuo and taken up in $Et_2O$. The bis-HCl salt of the amine was precipitated by the addition of HCl in $Et_2O$, and recrystallized from hexane/$Et_2O/CH_2Cl_2$ to provide 3.363 g of product as the bis-salt, m.p. 195°–198° C., homogeneous by TLC.

ANALYSIS: Calculated for $C_{27}H_{33}FN_4OS.2HCl$: 58.57%C; 6.37%H; 10.12%N. Found: 58.32%C; 6.45%H; 10.14%N.

EXAMPLE 52

3-[4-[1-(1,2-Benzisothiazol-3-yl)-4-piperazinyl]butyl]-2,2,5,5-tetramethyl-4-thiazolidinone hydrochloride hemihydrate A mixture of 3-(4-bromobutyl)-2,2,5,5-tetramethyl-4-thiazolidinone (4.00 g), 1-(1,2-benzisothiazol-3-yl)-piperazine hydrochloride (3.82 g), $K_2CO_3$ (6.58 g), NaI (300 mg) and acetonitrile (190 ml) was heated at 80° C. (oil bath temperature) under nitrogen. After 14 hours, TLC analysis (silica 25% EtOAc/hexane) showed the starting bromide to be absent, $R_f=0.39$. The reaction mixture was cooled to room temperature, ethyl acetate (100 ml) was added, and the mixture filtered. The filtrate was concentrated in vacuo to an oil. The oil was dissolved in ethyl acetate causing a solid to precipitate. The resulting mixture was filtered and the filtrate concentrated in vacuo to 6.65 g of oil which was purified by HPLC (silica gel 4% methanol/methylene chloride) to give 5.20 g of an oil ($R_f=0.29$ major and $R_f=0.36$ trace, 3% MeOH/$CH_2Cl_2$, two elutions).

The oil was dissolved in ethyl acetate/diethylether and the solution acidified with a HCl/diethylether solution until pH=2. The resulting salt was collected and dried to give 5.00 g of powder. The powder was recrystallized twice from ethanol/ethyl acetate yielding 2.65 g of fine needles, m.p. 218°–221° C.

ANALYSIS: Calculated for $C_{22}H_{32}N_4OS_2.HCl.0.5-H_2O$: 55.27%C; 7.17%H; 11.72%N; 7.42%Cl. Found: 55.31%C; 7.28%H; 11.65%N; 7.73%Cl.

EXAMPLE 53

3-[4-[1-(Benzo[b]thiophen-3-yl)-4-piperazinyl]butyl]-1-thia-3-azaspiro[4.4]nonan-4-one maleate A mixture of 3-(4-bromobutyl)-1-thia-3-azaspiro[4.4]-nonan-4-one (3.70 g), 3-piperazinyl benzo[b]thiophene (3.10 g), $K_2CO_3$ (7.00 g), NaI (300 mg) and acetonitrile (220 ml) was stirred at 35° C. under nitrogen. After 18 hours, TLC analysis showed the starting biomide ($R_f=0.46$: silica gel, 40% ethyl acetate/hexanes) to be absent. The mixture was cooled to ambient temperature, ethyl acetate (150 ml) was added, the inorganics filtered, and the filtrate concentrated under reduced pressure. The residue was taken up in dichloromethane (220 ml), washed successively with $H_2O$ (110 ml) and brine (130 ml), dried ($Na_2SO_4$) and concentrated to a foam. The foam was chromatographed on silica gel (450 g), eluting with 5% methanol in dichloromethane, to afford 3.62 g of a foam ($R_f=0.31$, 5% methanol/dichloromethane) which solidified upon addition of ether. The solid (mp: 99°–102° C.) was dissolved in ethanol (40 ml)/ether (230 ml) and the solution acidified by the addition of a saturated maleic acid/ether solution. The resulting salt (4.01 g) was recrystallized from ethanol/ethyl acetate to yield 2.83 g of powder, m.p. 177°–180° C.

ANALYSIS: Calculated for $C_{27}H_{35}N_3O_5S_2$: 59.43%C; 6.46%H; 7.70%N. Found: 59.33%C; 6.41%H; 7.67%N.

EXAMPLE 54

3-[4-[1-(1-Phenyl-1H-indol-3-yl)-4-piperazinyl]butyl]-2-methyl-1-thia-3-azaspiro[4.4]nonan-4-one dihydrochloride A mixture of 3-(4-bromobutyl)-2-methyl-1-thia-3-azaspiro[4.4]nonan-4-one (6.80 g), 1-(1-phenyl-1H-indol-3-yl)piperazine dihydrochloride (4.80 g), diisopropylethyl amine (8.16 g), $K_2CO_3$ (9.50 g), NaI (400 mg) and $CH_3CN$ (200 ml) was heated at 80° C. under nitrogen for 24 hours. The mixture was cooled and filtered, the inorganics were washed with dichloromethane, and the filtrate was concentrated under reduced pressure to a residue. The residue was diluted with 0.5N NaOH (150 ml) and the aqueous mixture extracted with ether (3×100 ml). The combined ether extracts were washed successively with $H_2O$ (150 ml) and brine (150 ml), dried ($Na_2SO_4$), and concentrated in vacuo. The crude product was chromatographed on silica gel, eluting with a gradient of 5–10% methanol in dichloromethane. The fractions containing the desired product ($R_f=0.42$, 10% methanol in dichloromethane) were concentrated to afford 4.84 g of a viscous liquid. The salt of this amine was precipitated from ether by the addition of ethereal HCl. A 4.74 g portion of the salt was recrystallized from ethanol yielding 2.15 g of solid, m.p. 214°–217° C.

ANALYSIS: Calculated for $C_{30}H_{38}N_4OS.2HCl$: 62.60%C; 7.00%H; 9.73%N. Found: 62.58%C; 6.95%H; 9.69%N.

EXAMPLE 55

3-[4-[1-(Benzo[b]thiophen-3-yl)-4-piperazinyl]butyl]-1-thia-3-azaspiro[4.5]decan-4-one maleate A mixture of 3-(4-bromobutyl)-1-thia-3-azaspiro[4.5]decan-4-one (4.47 g), 3-piperazinylbenzo[b]thiophene (3.50 g), $K_2CO_3$ (6.67 g), NaI (300 mg) and acetonitrile (210 ml) was heated at 70° C. under nitrogen. After 17 hours, TLC analysis showed a trace of the starting bromide ($R_f=0.41$, 40% ethyl acetate/hexanes, silica gel). The mixture was cooled to ambient temperature, ethyl acetate (150 ml) was added, the inorganics filtered, and the filtrate concentrated under reduced pressure. The residue was taken up in dichloromethane (220 ml), washed successively with $H_2O$ (140 ml) and brine (150 ml), dried ($Na_2SO_4$), and concentrated to a viscous liquid. The liquid was chromatographed on silica gel, eluting with 5% methanol in dichloromethane, to afford 4.50 g of viscous liquid ($R_f=0.33$, 5% methanol/dichloromethane, silica gel). The liquid was dissolved in ether and the solution acidified with a saturated maleic acid/ether solution to give 5.00 g of a salt. The salt was recrystallized from ethanol/ethyl acetate yielding 3.58 g of a fluffy solid, m.p. 191°–192° C. (dec.).

ANALYSIS: Calculated for $C_{24}H_{33}N_3OS_2.C_4H_4O_4$: 60.08%C; 6.66%H; 7.51%N. Found: 59.96%C; 6.57%H; 7.51%N.

EXAMPLE 56

3-[4-[1-(1-Phenyl-1H-indol-3-yl)-4-piperazinyl]butyl]-1-thia-3-azaspiro[5.4]decan-4-one dihydrochloride A mixture of 3-(4-bromobutyl)-1-thia-3-azaspiro[5.4]decan-4-one (4.00 g), 1-(1-phenyl-1H-indol-3-yl)piperazine (1.20 g), $K_2CO_3$ (6.50 g), NaI (300 mg) and acetonitrile (330 ml) was heated under nitrogen at 80° C. After 38 hours the mixture was cooled to ambient temperature and filtered, and the filtrate was concentrated under reduced pressure. The residue was taken up in dichloromethane, washed successively with $H_2O$ (150 ml) and brine (150 ml), dried ($Na_2SO_4$), and concentrated to a liquid. The liquid was chromatographed on silica gel, eluting with 5 to 10% methanol in dichloromethane, affording 2.73 g of liquid. The liquid was dissolved in ethanol and the salt of the amine precipitated by the addition of ethereal HCl to afford 1.90 g of solid. Recrystallization from ethanol gave 1.13 g of powder, m.p. 158° C. (begin decomposition).

ANALYSIS: Calculated for $C_{30}H_{38}N_4OS.2HCl$: 62.60%C; 7.00%H; 9.73%N. Found: 62.36%C; 6.86%H; 9.70%N.

EXAMPLE 57

3-[4-[1-[1-(4-Fluorophenyl)-1H-indol-3-yl]-4-piperazinyl]butyl]-1-thia-3-azaspiro[4.5]decan-4-one A mixture of 3-(4-bromobutyl)-1-thia-3-azaspiro[4.5]decan-4-one (3.8 g), 1-(4-fluorophenyl)-3-piperazino-1H-indole (3.7 g), $K_2CO_3$ (3.5 g), NaI (200 mg) and anhydrous $CH_3CN$ (150 ml) was heated to 80° C. with stirring under nitrogen. After 18 hours, no starting amine remained as judged by TLC. The mixture was cooled to room temperature and filtered, and the filtrate concentrated in vacuo. The residue was chromatographed on silica using EtOAc as an eluent. The fractions containing the desired product were combined and concentrated to provide 2.816 g of crystals, m.p. 134°–136° C., homogeneous by TLC.

ANALYSIS: Calculated for $C_{30}H_{37}FN_4OS$: 69.20%C; 7.16%H; 10.76%N. Found: 69.09%C; 7.14%H; 10.62%N.

EXAMPLE 58

3-(4-Bromobutyl)-5-methyl-4-thiazolidinone

As an alternative to the method described in Example 7, the title compound was prepared in the following manner:

To a −74° C. solution of 3-(4-bromobutyl)-4-thiazolidinone (5.20 g) and THF (70 ml) under nitrogen was rapidly added lithium bis(trimethylsilyl)amide (0.023 mole) in THF (23 ml) followed immediately by methyliodide (7.74 g). The resulting solution was stirred for 20 minutes (cooled by the $CO_2$/isopropanol bath), allowed to warm to −40° C., and acidified with 1N HCl (200 ml). The resulting aqueous mixture was extracted with 25% benzene/ether (3×100 ml). The combined extracts were washed with brine (200 ml), dried ($Na_2SO_4$), and concentrated in vacuo to a liquid which was chromatographed on silica gel, eluting with 45% ethyl acetate in hexanes, yielding 3.84 g of an oil. The oil was distilled to give 2.60 g of a colorless liquid, b.p. 123°–125° C. at 0.20 mmHg.

ANALYSIS: Calculated for $C_8H_{14}BrNOS$: 38.10%C; 5.60%H; 5.55%N. Found: 38.12%C; 5.58%H; 5.48%N.

EXAMPLE 59

3-(4-(1-[1,2-Benzisothiazol-3-yl]-4-piperazinyl)butyl-5-(2-hydroxyisopropyl)-4-thiazolidinone A mixture of 3-(4-bromobutyl)-5-(2-hydroxyisopropyl)-4-thiazolidinone (4.00 g), 3-piperazinyl-1,2-benzisothiazol hydrochloride (3.80 g), $K_2CO_3$ (8.00 g), NaI (450 mg), and acetonitrile (200 ml) was heated at 80° C. under nitrogen. After 17 hours the mixture was filtered, the insolubles were washed with dichloromethane, and the filtrate was concentrated in vacuo. The residue was taken up in dichloromethane (200 ml), washed successively with 5% NaOH (100 ml) and $H_2O$ (100 ml), and dried. Evaporation of the solvent at reduced pressure gave a viscous liquid. The crude product was chromatographed on silica gel. Elution with 8% methanol in dichloromethane gave 5.06 g of liquid. The HCl salt of this amine was prepared and recrystallized from ethanol/ethyl acetate to afford 2.26 g of a fine crystalline solid, m.p. 147°–150°.

ANALYSIS: Calculated for $C_{20}H_{30}N_4O_2S_2.HCl$: 53.54%C; 6.63%H; 11.89%N. Found: 53.31%C; 6.53%H; 11.80%N.

EXAMPLE 60

3-(4-(1-(1,2-Benzisothiazol-3-yl)-4-piperazinyl)butyl-spiro[1H-indene-2,5-thiazolidine]-2,3-dihydro-4-one A mixture of 3-(4-bromobutyl)-spiro[1H-indene-2,5-thiazolidine]-2,3-dihydro-4-one (4.00 g), 1-(1,2-benzisothiazol-3-yl)piperazine hydrochloride (3.31 g), $K_2CO_3$ (7.20 g), NaI (350 mg), and acetonitrile was heated at 80° C. under nitrogen. After 17 hours, the mixture was filtered, the insolubles washed with dichloromethane (120 ml), and the filtrate concentrated under reduced pressure. The residue was taken up in dichloromethane (225 ml), washed successively with 0.5 on NaOH (125 ml), $H_2O$ (125 ml) and brine (125 ml), and thereafter dried ($Na_2SO_4$), and concentrated to a foam. The foam was purified by repeated chromatography on silica gel, eluting with 8% methanol in dichloromethane, to give 3.50 g of solid. The HCl salt of this amine was prepared and recrystallized repeatedly from ethanol/ethyl acetate to affor 1.03 g of solid, m.p. 192°–195° C.

ANALYSIS: Calculated for $C_{26}H_{30}N_4OS_2.HCl$: 60.62%C; 6.07%H; 10.88%N. Found: 60.05%C; 6.13%H; 10.69%N.

EXAMPLE 61

3-(4-(1-[1,2-Benzisothiazol-3-yl]-4-piperazinyl)butyl)-5-methyl-4-thiazolidinone A mixture of 3-(4-bromobutyl)-5-methyl-4-thiazolidinone (4.00 g), 1-(1,2-benzisothiazol-3-yl)piperazine hydrochloride (4.46 g), $K_2CO_3$ (8.00 g) and NaI (300 mg) in acetonitrile (210 ml) was heated at 40°–45° C. for 64 hours and the product was processed in substantially the same manner as in Example 10 to afford 3.64 g of crystals, m.p. 113°–115° C.

ANALYSIS: Calculated for $C_{19}H_{26}N_4OS_2$: 58.43%C; 6.71%H; 14.34%N. Found: 58.32%C; 6.69%H; 14.29%N.

EXAMPLE 62

3-(4-(1-(6-Fluorobenzo[b]thiophen-3-yl)-4-piperazinyl)butyl)-5-(2-hydroxyisopropyl)-4-thiazolidinone maleate A mixture of 3-(4-bromobutyl)-5-(2-hydroxyisopropyl)-4-thiazolidinone (5.00 g), 1-(6-fluorobenzo[b]thiophen-3-yl)piperazine (4.44 g), $K_2CO_3$ (8.20 g) and NaI (400 mg) in acetonitrile (200 ml) was heated at 75° C. for 16 hours and the product was processed in substantially the same manner as in Example 10 to afford 2.35 g of crystalline solid, m.p. 159°–161° C.

ANALYSIS: Calculated for $C_{22}H_{30}FN_3O_2S_2.C_4H_4O_4$: 55.01%C; 6.04%H; 7.40%N. Found: 54.92%C; 5.99%H; 7.41%N.

EXAMPLE 63

3-(4-(1-(1,2-Benzisothiazol-3-yl)-4-piperazinyl)butyl)-5-(2,2,2-trifluoroethyl)-4-thiazolidinone hydrochloride A mixture of 3-(4-bromobutyl)-5-(2,2,2-trifluoroethyl)-4-thiazolidinone (3.20 g), 1-(1,2-benzisothiazol-3-yl)piperazine hydrochloride (2.81 g), $K_2CO_3$ (4.83 g) and NaI (250 mg) in acetonitrile (280 ml) was heated at 70° C. for 15 hours and the product was processed in substantially the same manner as in Example 10 to afford 2.30 g of crystals, m.p. 188°-200° C.

ANALYSIS: Calculated for $C_{20}H_{25}F_3N_4OS_2.HCl$: 48.52%C; 5.29%H; 11.32%N; 7.16%Cl. Found: 48.51%C; 5.32%H; 11.20%N; 7.28%Cl.

EXAMPLE 64

3-(4-(1-(3-Methylphenyl)-4-piperazinyl)-butyl)-5,5-dimethyl-4-thiazolidinone dihydrochloride A mixture of 3-(4-bromobutyl)-5,5-dimethyl-4-thiazolidinone (4.00 g), 1-(3-methylphenyl)piperazine (3.43 g), $K_2CO_3$ (8.31 g) and NaI (270 mg) in acetonitrile (180 ml) was heated at 75° C. for 17 hours and the product was processed in substantially the same manner as in Example 10 to afford 2.10 g of needles, m.p. 145° C. (begin decomposition).

ANALYSIS: Calculated for $C_{20}H_{31}N_3OS.2HCl$: 55.29%C; 7.66%H; 9.67%N; 16.32%Cl. Found: 55.06%C; 7.68%H; 9.62%N; 16.29%Cl.

EXAMPLE 65

3-(4-(1-(6-Fluorobenzo[b]thiophen-3-yl)piperazinyl)-butyl)-2,5,5-trimethyl-4-thiazolidinone maleate A mixture of 3-(4-bromobutyl)-2,5,5-trimethyl-4-thiazolidinone (4.00 g), 1-(6-fluorobenzo[b]thiophen-3-yl)piperazine (3.71 g), $K_2CO_3$ (6.00 g) and NaI (400 mg) in acetonitrile was heated at 50° C. for 16 hours and the product was processed in substantially the same manner as in Example 10 to afford 2.09 g of solid, m.p. 170°-174° C.

ANALYSIS: Calculated for $C_{22}H_{30}N_3FOS_2.C_4H_4O_4$: 56.60%C; 6.21%H; 7.62%N. Found: 56.57%C; 6.24%H; 7.62%N.

EXAMPLE 66

3-(4-(1-(6-Chlorobenzo[b]thiophen-3-yl)-4-piperazinyl)-butyl)-2,5,5-trimethyl-4-thiazolidinone hydrochloride A mixture of 3-(4-bromobutyl)-2,5,5-trimethyl-4-thiazolidinone (5.00 g), 6-chloro-3-piperazinylbenzo[b]thiophene (5.41 g), $K_2CO_3$ (8.63 g) and NaI (400 mg) in acetonitrile (200 ml) was heated at 90° C. for 16.5 hours and the product was processed in substantially the same manner as in Example 10 to afford 2.25 g of powder, m.p. 199°-202° C.

ANALYSIS: Calculated for $C_{22}H_{30}ClN_3OS_2HCl$: 54.09%C; 6.40%H; 8.60%N. Found: 53.67%C; 6.31%H; 8.60%N.

EXAMPLE 67

3-(4-(1-[1-Phenyl-1H-indol-3-yl]-4-piperazinyl)butyl)-2,5,5-trimethyl-4-thiazolidinone dihydrochloride A mixture of 3-(4-bromobutyl)-2,5,5-trimethyl-4-thiazolidinone (5.00 g), 1-(1-phenyl-1H-indol-3-yl)piperazine dihydrochloride (7.80 g), N,N-diisopropylethylamine (9.65 g), NaI (350 mg) in acetonitrile (250 ml) was heated at 75° C. for 17 hours and the product was processed in substantially the same manner as in Example 10 to afford 2.80 g of crystals, m.p. 217°-219° C.

ANALYSIS: Calculated for $C_{28}H_{36}N_4OS.2HCl$: 61.19%C; 6.97%H; 10.19%N. Found: 61.11%C; 6.91%H; 10.18%N.

EXAMPLE 68

3-(4-(1-(1-(4-Fluorophenyl)-1H-indol-3-yl)-4-piperazinyl)butyl)-2,5,5-trimethyl-4-thiazolidinone dihydrochloride hemihydrate A mixture of 3-(4-bromobutyl)-2,5,5-trimethyl-4-thiazolidinone (4.46 g), 1-(4-fluorophenyl)-3-piperazino-1H-indole (4.7 g), $K_2CO_3$ (4.4 g) and NaI (200 mg) in acetonitrile (175 ml) was heated at 80° C. for 18 hours and the product was processed in substantially the same manner as in Example 10 to afford 3.29 g of product, m.p. 182°-185° C.

ANALYSIS: Calculated for $C_{28}H_{35}FN_4OS.2HCl.0.5H_2O$: 58.32%C; 6.64%H; 9.71%N. Found: 58.11%C; 6.35%H; 9.72%N.

EXAMPLE 69

3-(4-(1-[1,2-Benzisothiazol-3-yl]-4-piperazinyl)butyl)-2,5,5-trimethyl-4-thiazolidinone hydrochloride A mixture of 3-(4-bromobutyl)-2,5,5-trimethyl-4-thiazolidinone (4.70 g), 1-(1,2-benzisothiazol-3-yl)piperazine 1-(1,2-benzisothiazol-3-yl)piperazine hydrochloride (4.72 g), $K_2CO_3$ (8.13 g) and NaI (300 mg) in acetonitrile (200 ml) was heated at 65° C. for 16 hours and the product was processed in substantially the same manner as in Example 10 to afford 2.77 g of crystals, m.p. 209°-214° C.

ANALYSIS: Calculated for $C_{21}H_{30}N_4OS_2.HCl$: 55.43%C; 6.87%H; 12.31%N; 7.79%Cl. Found: 55.26%C; 6.82%H; 12.30%N; 7.97%Cl.

EXAMPLE 70

3-[4-[1-(6-Chloro-1,2-benzisothiazol-3-yl)-4-piperazinyl]butyl]-2,5,5-trimethyl-4-thiazolidinone hydrochloride A mixture of 3-(4-bromobutyl)-2,5,5-trimethyl-4-thiazolidinone (3.6 g), 6-chloro-1,2-benzisothiazol-3-yl piperazine (3.7 g), $K_2CO_3$ (4.0 g) and NaI (200 mg) in $CH_3CN$ (175 ml) was heated at 80° C. for 18 hours and the product was processed in substantially the same manner as in Example 10 to afford 4.714 g of product, m.p. 204°-206° C.

ANALYSIS: Calculated for $C_{21}H_{29}N_4OS_2.HCl$: 51.53%C; 6.18%H; 11.44%N. Found: 51.45%C; 6.12%H; 11.48%N.

EXAMPLE 71

3-(4-(1-[3-methylphenyl]-4-piperazinyl)butyl)-2,2,5,5-tetramethyl-4-thiazolidinone dihydrochloride A mixture of 3-(4-bromobutyl)-2,2,5,5-tetramethyl-4-thiazolidinone (3.80 g), 1-(3-methylphenyl)piperazine (2.60 g), $K_2CO_3$ (6.42 g) and NaI (400 mg) in acetonitrile (200 ml) was heated at 80° C. for 16 hours and the product was processed in substantially the same manner as in Example 10 to afford 2.96 g of needles, m.p. 182° C. (begin decomposition).

ANALYSIS: Calculated for $C_{22}H_{35}N_3OS.2HCl$: 57.13%C; 8.06%H; 9.08%N; 15.33%Cl. Found: 56.92%C; 8.00%H; 8.93%N; 15.38%Cl.

EXAMPLE 72

3-(4-(1-(2-Methoxyphenyl)-4-piperazinyl)butyl)-2,2,5,5-tetramethyl-4-thiazolidinone dihydrochloride A mixture of 3-(4-bromobutyl)-2,2,5,5-tetramethyl-4-thiazolidinone (3.60 g), 1-(2-methoxyphenyl)piperazine (2.59 g), $K_2CO_3$ (5.90 g) and NaI (320 mg) in acetonitrile (190 ml) was heated at 90° C. for 14 hours and the product was processed in substantially the same manner as in Example 10 to afford 2.43 g of solid, m.p. 138° C. (being decomposition).

ANALYSIS: Calculated for $C_{22}H_{37}Cl_2N_3O_2S$: 55.22%C; 7.79%H; 8.78%N; 14.82%Cl. Found: 54.98%C; 7.69%H; 8.75%N; 14.95%Cl.

EXAMPLE 73

3-(4-(1-(2-Methoxyphenyl)-4-piperazinyl)butyl)-1-thia-3-azaspiro[4.4]nonan-4-one dihydrochloride A mixture of 3-(4-bromobutyl)-1-thia-3-azaspiro[4.4]nonan-4-one (4.60 g), 1-(2-methoxyphenyl)piperazine (3.33 g), $K_2CO_3$ (5.42 g) and NaI (310 mg) in acetonitrile (200 ml) was heated at 65° C. for 6 hours and the product was processed in substantially the same manner as in Example 10 to afford 3.43 g of crystals, m.p. 144° C. (begin decomposition).

ANALYSIS: Calculated for $C_{22}H_{33}N_3O_2S.2HCl$: 55.45%C; 7.40%H; 8.82%N; 14.88%Cl. Found: 55.54%C; 7.40%H; 8.80%N; 14.54%Cl.

EXAMPLE 74

3-(4-(1-(Benzo[b]thiophen-3-yl)-4-piperazinyl)butyl)-1-thia-3-azaspiro[4.4]nonan-4-one maleate A mixture of 3-(4-bromobutyl)-1-thia-3-azaspiro[4.4]-nonan-4-one (3.70 g), 3-piperazinyl benzo[b]thiophene (3.10 g), $K_2CO_3$ (7.00 g) and NaI (300 mg) in acetonitrile (220 ml) was heated at 35° C. for 18 hours and the product was processed in substantially the same manner as in Example 10 to afford 2.83 g of powder, m.p. 177°–180° C.

ANALYSIS: Calculated for $C_{27}H_{35}N_3O_5S_2$: 59.43%C; 6.46%H; 7.70%N. Found: 59.33%C; 6.41%H; 7.67%N.

EXAMPLE 75

3-[4-[1-(1,2-Benzisothioazol-3-yl)-4-piperazinyl]butyl]-1-thia-3-azaspiro[4.4]nonan-4-one A mixture of 3-(4-bromobutyl)-1-thia-3-azaspiro[4.4]-nonan-4-one (4.50 g), 1-(1,2-benzisothiazol-3-yl)piperazine hydrochloride (4.33 g), $K_2CO_3$ (7.45 g) and NaI (560 mg), in acetonitrile (220 ml) was heated at 65° C. for 14.5 hours and the product was processed in substantially the same manner as in Example 10 to afford 2.25 g of crystals, m.p. 200°–203° C.

ANALYSIS: Calculated for $C_{22}H_{30}N_4OS_2.HCl$: 56.57%C; 6.69%H; 11.99%N; 7.59%Cl. Found: 56.15%C; 6.75%H; 12.11%N; 7.88%Cl.

EXAMPLE 76

3-(4-(1-(1,1-dioxo-1,2-Benzisothiazol-3-yl)-4-piperazinyl)butyl)-1-thia-3-azaspiro[4.4]nonan-4-one A mixture of 3-(4-bromobutyl)-1-thia-3-azaspiro[4.4]-nonan-4-one (3.50 g), 1-(1,1-dioxo-1,2-benzisothiazol-3-yl)piperazine (3.30 g), $K_2CO_3$ (4.98 g) and NaI (280 mg) in acetonitrile (230 ml) was heated at 85° C. for 20 hours and the product was processed in substantially the same manner as in Example 10 to afford 2.89 g of needles, m.p. 137°–140° C.

ANALYSIS: Calculated for $C_{22}H_{30}N_4O_3S_2$: 57.12%C; 6.54%H; 12.11%N. Found: 57.24%C; 6.57%H; 12.12%N.

EXAMPLE 77

3-(4-(1-(6-Fluorobenzo[b]thiophen-3-yl)-4-piperazinyl)-butyl)-2-methyl-3-azaspiro[4.4]nonan-4-one maleate A mixture of 3-(4-bromobutyl)-2-methyl-3-azaspiro[4.4]-nonan-4-one (5.00 g), 6-fluoro-3-piperazinylbenzo[b]thiophene (4.55 g), $K_2CO_3$ (8.00 g) and NaI (0.400 mg) in acetonitrile was heated at 80° C. for 2.5 hours and the product was processed in substantially the same manner as in Example 10 to afford 4.38 g of solid, m.p. 174°–176° C.

ANALYSIS: Calculated for $C_{24}H_{32}FN_3OS_2.C_4H_4O_4$: 58.21%C; 6.28%H; 7.27%N. Found: 57.93%C; 6.20%H; 7.23%N.

EXAMPLE 78

3-(4-(1-(6-Chlorobenzo[b]thiophen-3-yl)-4-piperazinyl)-butyl)-2-methyl-1-thia-3-azaspiro[4.4]nonan-4-one hydrochloride A mixture of 3-(4-bromobutyl)-2-methyl-1-thia-3-azaspiro[4.4]nonan-4-one (5.00 g), 6-chloro-3-piperazinylbenzo[b]thiophene (5.10 g), $K_2CO_3$ (8.00 g) and NaI (400 mg) in acetonitrile (250 ml) was heated at 85° C. for 15.5 hours and the product was processed in substantially the same manner as in Example 10 to afford 1.43 g of crystalline solid, m.p. 211°–214° C.

ANALYSIS: Calculated for $C_{24}H_{32}ClN_3OS_2.HCl$: 56.02%C; 6.46%H; 8.17%N. Found: 55.81%C; 6.50%H; 8.24%N.

EXAMPLE 79

3-(4-(1-(1,2-Benzisothiazol-3-yl)-4-piperazinyl)butyl)-2-methyl-1-thia-3-azaspiro[4.4]nonan-4-one hydrochloride A mixture of 3-(4-bromobutyl)-2-methyl-1-thia-3-azaspiro[4.4]nonan-4-one (3.84 g), 1-(1,2-benzisothiazol-3-yl)piperazine hydrochloride (3.49 g), $K_2CO_3$ (5.90 g) and NaI (280 mg) in acetonitrile (215 ml) was heated at between 65°–80° C. for 16.5 hours and the product was processed in substantially the same manner as in Example 10 to afford 2.86 g of crystals, m.p. 210°–215° C.

ANALYSIS: Calculated for $C_{23}H_{32}N_4OS_2.HCl$: 57.42%C; 6.91%H; 11.64%N; 7.37%Cl. Found: 57.21%C; 6.87%H; 11.63%N; 7.03%Cl.

EXAMPLE 80

3-(4-(1-[1,2-Benzisothiazol-3-yl]-4-piperazinyl)butyl)-1-thia-3-azaspiro[4.5]decan-4-one A mixture of 3-(4-bromobutyl)-1-thia-3-azaspiro[4.4]-nonan-4-one (4.00 g), 1-(1,2-benzisothiazol-3-yl)piperazine hydrochloride (3.67 g), $K_2CO_3$ (7.00 g) and NaI (300 mg) in acetonitrile (220 ml) was heated at 70° C. for 20 hours and the product was processed in substantially the same manner as in Example 10 to afford 3.01 g of crystalline solid, m.p. 209° C.

ANALYSIS: Calculated for $C_{23}H_{32}N_4OS_2.HCl$: 57.42%C; 6.91%H; 11.64%N; 7.37%Cl. Found: 57.51%C; 6.82%H; 11.75%N; 7.30%Cl.

EXAMPLE 81

3-[4-[1-(6-Chloro-1,2-benzisothiazol-3-yl)-4-piperazinyl]butyl]-1-thia-3-azaspiro[4.5]decan-4-one hydrochloride A mixture of 3-(4-bromobutyl)-1-thia-3-azaspiro[4.5]-]decanone (2.7 g), 6-chloro-1,2-benzisothiazol-3-yl piperazine (2.0 g), $K_2CO_3$ (2.2 g) and NaI (200 mg) in acetonitrile (100 ml) was heated at 80° C. for 8 hours and the product was processed in substantially the same manner as in Example 10 to afford 1.557 g of solid, m.p. 202°–205° C.

ANALYSIS: Calculated for $C_{23}H_{31}N_4OS_2Cl\cdot HCl$: 53.58%C; 6.26%H; 10.87%N. Found: 53.54%C; 6.20%H; 10.85%N.

EXAMPLE 82

3-(4-Bromobutyl)-2,5,5-trimethyl-4-thiazolidinone

To a −73° C. solution of 3-(4-bromobutyl)-2-methyl-4-thiazolidinone (6.00 g), methyliodide (10.99 g) and THF (50 ml) under nitrogen was added lithium bis(-trimethylsilyl)amide (0.0500 mol) in THF (50 ml) at a rate to maintain the internal temperature below −55° C. The resulting solution was stirred at <−55° C. for 10 minutes, allowed to warm to −40° C., and at which temperature 1N HCl (250 ml) was added. The aqueous mixture was extracted with 25% benzene/ether (3×125 ml). The combined extracts were washed with brine (200 ml), dried ($Na_2SO_4$), and concentrated to a liquid which was chromatographed on silica gel yielding 5.07 g of a liquid. The liquid was distilled to give 3.80 g of a clear liquid, b.p. 109°–114° C. at 0.20 mmHg.

ANALYSIS: Calculated for $C_{10}H_{18}BrNOS$: 42.86%C; 6.47%H; 5.00%N. Found: 42.93%C; 6.47%H; 5.00%N.

We claim:

1. A compound of the formula

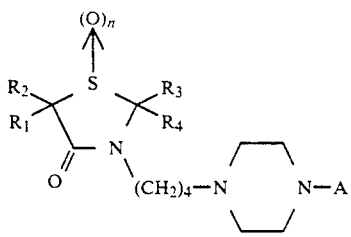

where n is 0 or 1; A is

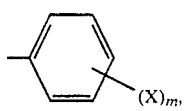

where X in each occurrence is independently hydrogen, halogen, loweralkyl, hydroxy, nitro, loweralkoxy, amino, cyano, trifluoromethyl or methylthio; m is 1 or 2; $R_1$ and $R_2$ are independently hydrogen, loweralkyl,

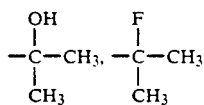

or aryl except that when $R_1$ is

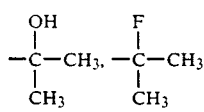

or aryl, $R_2$ is hydrogen, or alternatively $R_1+R_2$ taken together with the carbon atom to which they are attached form a cyclopentane, cyclohexane, cyclohep-tane, pyran, thiopyran, indan or piperidine ring; $R_3$ and $R_4$ are independently hydrogen or loweralkyl, or alternatively $R_3+R_4$ taken together with the carbon atom to which they are attached form a cyclopentane, cyclohexane, cycloheptane, pyran, thiopyran, pyrrolidine or piperidine ring, the term aryl signifying an unsubstituted phenyl group or a phenyl group substituted with 1, 2 or 3 substituents each of which being independently loweralkyl, loweralkoxy, hydroxy, halogen, loweralkythio, cyano, amino or trifluoromethyl, or a pharmaceutically acceptable acid addition salt thereof.

2. The compound according to claim 1, where n=0.

3. The compound according to claim 1, where $R_1=R_2=H$.

4. The compound according to claim 1, where $R_1+R_2=-(CH_2)_4-$.

5. The compound according to claim 1, where $R_1=R_2=CH_3$.

6. The compound according to claim 1, where

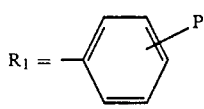

where P is hydrogen, loweralkyl, loweralkoxy, hydroxy, loweralkylthio or amino and $R_2$ is hydrogen.

7. The compound according to claim 1, where $R_3$ and $R_4$ are independently hydrogen or loweralkyl.

8. The compound according to claim 2, where $R_1=R_2=H$.

9. The compound according to claim 2, where $R_1+R_2=-(CH_2)_4-$.

10. The compound according to claim 2, where $R_1=R_2=CH_3$.

11. The compound according to claim 2, where

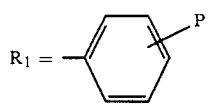

where P is hydrogen, loweralkyl, loweralkoxy, hydroxy, loweralkylthio or amino and $R_2$ is hydrogen.

12. The compound according to claim 2, where $R_3$ and $R_4$ are independently hydrogen or loweralkyl.

13. The compound according to claim 1, which is 3-[4-[1-(2-methylphenyl)-4-piperazinyl]butyl]-4-thiazolidinone.

14. The compound according to claim 1, which is 3-[4-[1-(3-methylphenyl)-4-piperazinyl]butyl]-4-thiazolidinone.

15. The compound according to claim 1, which is 3-[4-[1-(2,3-dimethylphenyl)-4-piperazinyl]butyl]-4≠-thiazolidinone.

16. The compound according to claim 1, which is 3-[4-[1-(2-methoxyphenyl)-4-piperazinyl]butyl]-4-thiazolidinone.

17. The compound according to claim 1, which is 3-[4-[1-(3-methylphenyl)-4-piperazinyl]butyl]-4-thiazolidinone.

18. The compound according to claim 1, which is 3-[4-[1-(4-fluorophenyl)-4-piperazinyl]butyl]-4-thiazolidinone.

19. The compound according to claim 1, which is 3-[4-[1-(2-chlorophenyl)-4-piperazinyl]butyl]-4-thiazolidinone.

20. The compound according to claim 1, which is 3-[4-[1-(3-chlorophenyl)-4-piperazinyl]butyl]-4-thiazolidinone.

21. The compound according to claim 1, which is 3-[4-[1-(4-chlorophenyl)-4-piperazinyl]butyl]-4-thiazolidinone.

22. The compound according to claim 1, which is 3-[4-[1-(3-trifluoromethylphenyl)-4-piperazinyl]butyl]-4-thiazolidinone.

23. The compound according to claim 1, which is 3-[4-[1-(2-methoxyphenyl)-4-piperazinyl]butyl]-1,4-dioxothiazolidine.

24. The compound according to claim 1, which is 3-[4-[1-(4-fluorophenyl)-4-piperazinyl]butyl]-1,4-dioxo-thiazolidinone.

25. The compound according to claim 1, which is 3-[4-[1-(2-methoxyphenyl)-4-piperazinyl]butyl]-2-methyl-4-thiazolidinone.

26. The compound according to claim 1, which is 3-[4-[1-(4-fluorophenyl)-4-piperazinyl]butyl]-2-methyl-4-thiazolidinone.

27. The compound according to claim 1, which is 3-[4-[1-(3-chlorophenyl)-4-piperazinyl]butyl]-2-methyl-4-thiazolidinone.

28. The compound according to claim 1, which is 3-[4-[1-(2-methoxyphenyl)-4-piperazinyl]butyl]-5-methyl-4-thiazolidinone.

29. The compound according to claim 1, which is 2,2-dimethyl-3-[4-[1-(3-methylphenyl)-4-piperazinyl]butyl]-4-thiazolidinone.

30. The compound according to claim 1, which is 2,2-dimethyl-3-[4-[1-(2-methoxyphenyl)-4-piperazinyl]butyl]-4-thiazolidinone.

31. The compound according to claim 1, which is 2,2-dimethyl-3-[4-[1-(3-chlorophenyl)-4-piperazinyl]butyl]-4-thiazolidinone.

32. The compound according to claim 1, which is 2,2-dimethyl-3-[4-[1-(3-trifluoromethylphenyl)-4-piperazinyl]butyl]-4-thiazolidinone.

33. The compound according to claim 1, which is 2,2-dimethyl-3-[4-[1-(3-methylthiophenyl)-4-piperazinyl]butyl]-4-thiazolidinone.

34. The compound according to claim 1, which is 5,5-dimethyl-3-[4-[1-(2-methoxyphenyl)-4-piperazinyl]butyl]-4-thiazolidinone.

35. The compound according to claim 1, which is 5,5-dimethyl-3-[4-[1-(3-trifluoromethylphenyl)-4-piperazinyl]butyl]-4-thiazolidinone.

36. The compound according to claim 1, which is 5-phenyl-3-[4-[1-(3-trifluoromethylphenyl)-4-piperazinyl]butyl]-4-thiazolidinone.

37. The compound according to claim 1, which is 3-[4-[1-(3-trifluoromethylphenyl)-4-piperazinyl]butyl]-5,5-dimethyl-4-thiazolidinone.

38. The compound according to claim 1, which is 3-[4-[1-(2-methylphenyl)-4-piperazinyl]butyl]-5,5-dimethyl-4-thiazolidinone.

39. The compound according to claim 1, which is 3-[4-[1-(2,3-dimethylphenyl)-4-piperazinyl]butyl]-5,5-dimethyl-4-thiazolidinone.

40. The compound according to claim 1, which is 3-(4-(1-(3-methylphenyl)-4-piperazinyl)butyl)-5,5-dimethyl-4-thiazolidinone.

41. The compound according to claim 1, which is 3-(4-(1-[3-methylphenyl]-4-piperazinyl)butyl)-2,2,5,5-tetramethyl-4-thiazolidinone.

42. The compound according to claim 1, which is 3-(4-(1-(2-methoxyphenyl)-4-piperazinyl)butyl)-2,2,5,5-tetramethyl-4-thiazolidinone.

43. The compound according to claim 1, which is 3-(4-(1-(2-methoxyphenyl)-4-piperazinyl)butyl)-1-thia-3-azaspiro[4.4]nonan-4-one.

* * * * *